United States Patent [19]

Magnus

[11] Patent Number: 5,508,447
[45] Date of Patent: Apr. 16, 1996

[54] SHORT SYNTHETIC ROUTE TO TAXOL AND TAXOL DERIVATIVES

[75] Inventor: Philip D. Magnus, Austin, Tex.

[73] Assignee: Board of Regents, The University of Texas System, Austin, Tex.

[21] Appl. No.: 248,083

[22] Filed: May 24, 1994

[51] Int. Cl.$^6$ .............................................. C07D 313/06
[52] U.S. Cl. ........................................ 509/354; 549/214
[58] Field of Search ................................... 549/214, 354

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,296,506 | 3/1994 | Kingston et al. | 514/449 |
| 5,405,972 | 1/1994 | Holton et al. | 549/214 |
| 5,461,169 | 10/1995 | Nicolaou et al. | 549/510 |

OTHER PUBLICATIONS

March, J., "Advanced Organic Chemistry", 2nd ed., pp. 246–248, 1977.
Stu Borman, "Scientists Mobilize to Increase Supply of Anticancer Drug Taxol," *C&EN*, pp. 11–18, Sep. 1991.
Brieva et al., "Chemoenzymatic Synthesis of the C–13 Side Chain of Taxol; Optically–Active 3–Hydroxy–4–phenyl β–Lactam Derivatives," *J. Org. Chem.*, 58:1068–1075, 1993.
Marilyn Chase, "A New Cancer Drug May Extend Lives—At Cost of Rare Trees," *The Wall Street Journal*, Apr. 9, 1991.
Chen et al., "Taxol Structure–Activity Relationships: Synthesis and Biological Evaluation of 10–Deoxytaxol," *The Journal of Organic Chemistry*, 58(11):2927– 2928, 1993.
Chen., "Taxol Structure–Activity Relationships: Synthesis and Biological Evaluation of 2–Deoxytaxol," *Tetrahedron Letters*, 34(20):pp. 3205–3206, 1993.
Faye Flam, "Race to Synthesize Taxol Ends in a Tie," *Science*, vol. 263:p. 911, 1994.
Georg et al., "Asymmetric Synthesis of β–Lactams and N–Benzoyl–e–Phenylisoserines Via the Staudinger Reaction, " *Tetrahedron Letters, 32(27):pp. 3151–3154, 1991.*
Georg et al., "Galactose–Imines in the Staudinger Reaction," *Tetrahedron Letters*, 33(16):pp. 2111–2114, 1992.
Golinski et al., "An Enantioselective Approach to Ring of Taxol Using The Wieland–Miescher Ketone,"_0 *Tetrahedron Letters*, 34(1):pp. 55–58, 1993.
Gou et al., "A Practical Chemoenzymatic Synthesis of the Taxol C–13 Side Chain N–Benzoyl–(2R, 3S)–3–phenylisoserine," *J. Org. Chem.*, 58:pp. 1287–1289, 1993.
Holton et al., "First Total Synthesis of Taxol. 1. Functionalization of the B Ring," *J. Am. Chem. Soc.*, 116:pp. 1597–1598, 1994.
Jones et al., "An Asymmetric Synthesis of MK–0417. Observations on Oxazaborolidine–Catalyzed Reductions," *J. Org. Chem.*, 56–pp. 763–769, 1991.
Larry L. Klein, "Synthesis of 9–Dihydrotaxol: A Novel Bioactive Taxane," *Tetrahedron Letters*, 34(13):pp. 2047–2050, 1993.
Jubert and Knoche, "Preparation of New Classes of Aliphatic, Allylic, and Benzylic Zinc and Copper Reagents by the Insertion of Zinc Dust into Organic Halides, Phosphates, and Sulfonates," *J. Org. Chem.*, 57:pp. 5425–5431, 1992.
Magee et al., "A straightforward Route to Functionalized Intermediates Containing the CD of Taxol," *J. Org. Chem.*, 57(12):pp. 3274–3276, 1992.
Wender and Mucciaro, "A New and Practical Approach to the Synthesis of Taxol and Taxol Analogues: The Pinene Path," *J. Am. Chem. Soc., 114:pp. 5878–5879, 1992.*
Nicolaou et al., "A Convergent Strategy Towards Taxol. A Facile Enantioselective Entry Into a Fully Functionalized Ring a System," *J. Chem. Soc., Chem. Commun.*, pp. 1117–1118, 1992.
Nicolaou et al., "Total Synthesis of Taxol," *Nature*, 367:pp. 630–634, 1994.
Nicolaou et al., "Novel Chemistry of Taxol. Retrosynthetic and Synthetic Studies," *J. Chem. Soc., Chem. Commun., pp. 295–296, 1994.*
Nicolaou et al., "Synthesis of Novel Taxoids," *J. Am. Chem. Soc., 116:pp. 1591–1592, 1994.*
Ojima et al., "New and Efficient Approaches to the Semi-synthesis of Taxol and Its C–13 Side Chain Analogs by Means of β–Lactam Synthon Method," *Tetrahedron*, 48(34):pp. 6985–7012, 1992.
Wender and Rawlins, "Toward the Synthesis of the Taxol C,D. Ring System: Photolysis of α–Methoxy Ketones," *Tetrahedron*, 48(34):pp. 7033–7048, 1992.
Winkler and Subrahmanyam, "Studies Directed Towards the Synthesis of Taxol: Preparation of C–13 Oxygenated Taxane Congeners," *Tetrahedron*, 48(34):pp. 7049–7056, 1992.
Charles S. Swindell, "Taxane Diterpene Synthesis Strategies. A Review," *Organic Preparations and Procedures Int.*, pp. 465–543, 23(4), 1991.
Ojima et al., "Synthesis and Structure—Activity Relationships of Novel Nor–Seco Analogs of Taxol and Taxotere," *J. Org. Chem.*, 59:pp. 515–517, 1994.

(List continued on next page.)

*Primary Examiner*—C. Warren Ivy
*Assistant Examiner*—Ba K. Trinh
*Attorney, Agent, or Firm*—Arnold White & Durkee

[57] ABSTRACT

A short route to the total synthesis of the core skeleton of the taxol ring system is described. The same sequence of transformations can be carried out to make the 7-hydroxy series, and connect the additional carbon atoms required for the A-ring. The number of steps to the taxane skeleton is 13, making it the shortest route from readily available inexpensive starting materials.

1 Claim, 5 Drawing Sheets

OTHER PUBLICATIONS

Wang et al., "A Straightforward Approach to the Synthesis of the Tricyclic Core of Taxol," *J. Org. Chem., 58:pp. 2931–2932, 1993.*

Emmer and Weber-Roth, "Synthesis of Derivatives of FK 506 and FR 900520: Modifications at the Binding Domain," *Tetrahedron,* 48(28):pp. 5861–5874, 1992.

Borman, Stu, "Higher Yield Synthetic Route To Cyclic Enediynes Developed," *Chemical & Engineering,* Aug. 28, 1995:28–30.

Thayer, Ann, "Firms Dispute Cancer Drug Patent Rights," *Chemical & Engineering,* Oct. 30, 1995:8.

International Search Report, Sep. 29, 1995.

Taxane numbering

Taxol (R = COPh, R₁ = Ac)

SHORT SYNTHETIC ROUTE TO TAXOL AND TAXOL DERIVATIVES

BACKGROUND OF THE INVENTION

1. Field of the Invention

The invention relates to the chemical synthesis of taxol, taxol intermediates, taxol precursors and novel taxol related compounds accessible through these precursors. Also described are pharmaceutical compositions and methods of use of the new compounds that have taxol-like activity.

2. Description of Related Art

The synthesis of the diterpene alkaloid taxol has been a popular target for total synthesis for the past ten years; however, it is only recently that the need for a total synthesis has taken on a new urgency in view of its medical importance in breast cancer treatment (Time, 1991) and more recently a possible treatment in kidney disease (Pharmaceuticals & Biotech Daily, 1994). Taxol is in phase II/phase III clinical trials and is showing extremely promising activity, particularly against ovarian, breast and lung cancers (Rowinsky, et al., 1990). Taxol has several advantages over other antitumor agents currently in use, including its relative lack of toxicity compared to other antitumor agents such as vinblastine and vincristine. Consequently, taxol has become the focus of a large number of antitumor programs both in academia and in the pharmaceutical industry (Klingston, et al., 1990; Winkleer, 1992; Swindell, 1991). Unfortunately, this effort, intended to explore the full range of tumor response to taxol chemtherapy, is severely limited by the scarcity of taxol itself.

Taxol is isolated from the North American Yew tree but only in very small amounts, requiring a time-consuming purification. The yew tree is an environmentally protected species and cannot be considered a permanent source of taxol. Even if this were not the case, the total yew tree population is estimated to yield only enough taxol for approximately one year of clinical evaluation.

Even if Taxol supplies were abundant, it has become apparent that potency of the drug is relatively low so that there is a particular need to obtain quantities sufficient to develop more active derivatives and analogs of this promising drug. French researchers have recently claimed that certain derivatives of taxol such as taxotere are more potent than the parent (Mangatal, et al., 1989; Colin, et al., 1988).

Therapeutic protocols presently require dose levels of 500 mg per patient, making it even more imperative to develop alternate sources of the drug or to devise an efficient chemical synthesis. Current supplies are inadequate to afford treatment to all patients for whom this drug is indicated.

There is therefore a need to provide a chemical synthesis of taxol efficient enough to supply large quantities (>100 kilos), and flexible enough to provide analogs in order to explore structure activity relationships (SAR). Such structure activity relationships for taxol and taxotere are the subject of current research (see, for example, Ojima, et al., 1994). Analogs and derivatives of taxol offer potential for more effective treatment of breast cancer with the goal of developing more selectivity and higher potency. Additionally, as with most cancer therapy, resistance to treatment is usually encountered, creating a need for second and third generation derivatives of the active parent compound.

Currently, research groups attempting to develop a total or partial synthesis of taxol, while making some progress, have developed multistep syntheses on the order of thirty to forty steps (Borman, 1991). This is far too long to be of any real practical commercial use, as anything more than 25 steps is not considered to be practical (Science, 1994). The synthesis of taxol should be no more than about twenty steps, and it is essential that the synthesis be enantiospecific.

The synthesis of taxol is, however, complicated by its different functional groups, making it difficult to predict the effect of modifications in one part of the molecule on other positions. Recently, total synthesis of taxol has been reported (Holton, et al., 1994; Nicolaou, et al., 1994). While of scientific significance, these syntheses do not appear to be commercially viable routes to taxol because the number of synthetic steps is quite high and because overall yields are low (Science, 1994).

It is therefore desirable to develop a simple, efficient synthetic route to taxol. Intermediates along the route as well as the end product will provide compounds so as to be able to determine the effect of structure activity relationships. This will lead to improvements on the natural form of taxol and will provide a rational approach in reducing toxicity and increasing efficacy.

SUMMARY OF THE INVENTION

The present invention seeks to overcome these and other drawbacks inherent in the prior art by providing a relatively short, efficient synthesis of the core structure of taxol. The disclosed syntheses address all the issues of the large number of functional groups from the outset, and are not simply models on which to conduct research studies. Furthermore, the strategy is amenable to large scale operation, employing reactions and readily available reagents that can be used by process manufacture groups experienced in the pharmaceutical industry.

Most importantly, the synthesis involves relatively few steps considering the complexity of the molecule. As a general rule, the synthesis of a diterpene (20 carbon atoms in the core structure) is acceptable with twenty steps. The added complexity of the multiple oxygen functionality would be expected to add at least another ten steps, making a total of thirty steps. The present invention, utilizing readily available and inexpensive starting materials, provides a total synthesis of taxol in significantly fewer steps. As disclosed herein, total synthesis of the A/B/C taxol system is accomplished in 13 steps (see scheme 21). This contrasts with recently published total syntheses of taxol by two different groups; Holton, et al. (1994) and Nicolau, et al. (1994) that appear to require 45–50 steps if one assumes starting with simple, commercially available materials.

The present invention provides a commercially practible total synthesis of the A, B and C rings of taxol and allows for a wide variety of structural variations at positions 7, 8, 12, 16, and 17. Two major synthetic routes are described. The first involves ring expansion of seven-membered ring intermediate into an eight membered ring to provide ring B of taxol. In a second approach, B ring synthesis involves cyclopropanation of a seven-membered α,β-unsaturated ketone followed by reductive or nucleophilic opening of the internal cyclopropane bond to give the eight-membered B ring. The second strategy provides the eight-membered ring more directly. The taxane numbering system and the corresponding numbering system for taxol are shown in FIGS. 1A and 1B.

There are several advantages to the synthetic procedures described herein. A major advantage is that synthesis of the taxol A, B, C ring system does not require complex or expensive starting materials. The entire synthesis is possible from simple, inexpensive, and commercially available precursors. The starting materials referred to in scheme 2, i.e., the three-bromoester of propanoic acid and methacrylol chloride (or substituted analogs, e.g., the substitution of the methacrylol methyl group by alkyl or aryl groups) may be employed by selecting, for example, any of a relatively wide choice of α,β-unsaturated acid chlorides. The methyl or other R group provided by the acid chloride will ultimately provide the 19-substituent in the taxol system. Different protecting groups can be used other than t-butyldimethylsilyl. Such protecting groups are considered in the usual range of standard alcohol protecting groups and should be selected with the proviso that they are stable to subsequent aldol or Claisen reaction, lithium aluminum hydride reduction, and oxidative rearrangement. This would therefore exclude esters such as acetates, etc. These reactions are shown in Schemes 1–8.

Scheme 1

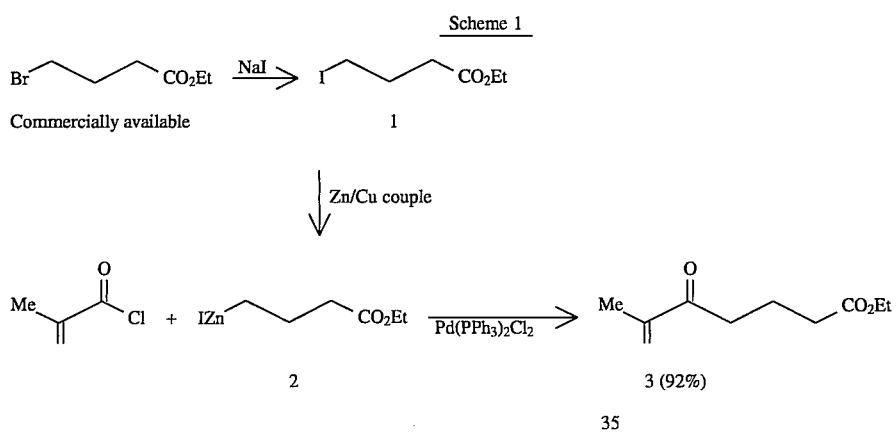

Scheme 2

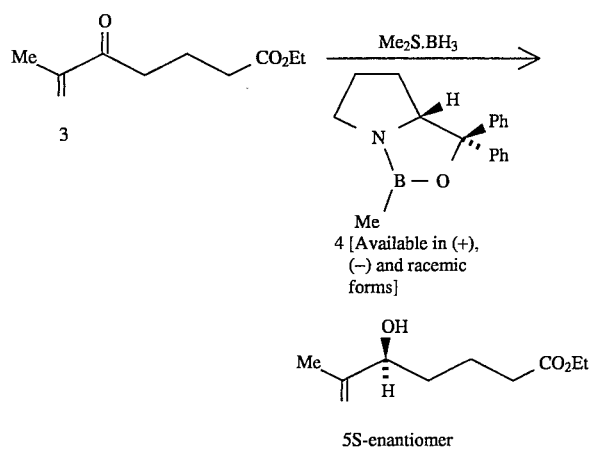

Scheme 3

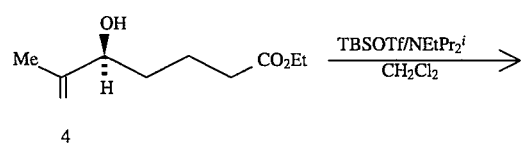

-continued
Scheme 3

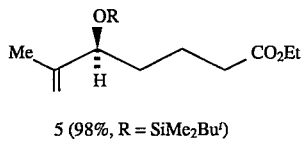

5 (98%, R = SiMe$_2$Bu$^t$)

Scheme 4

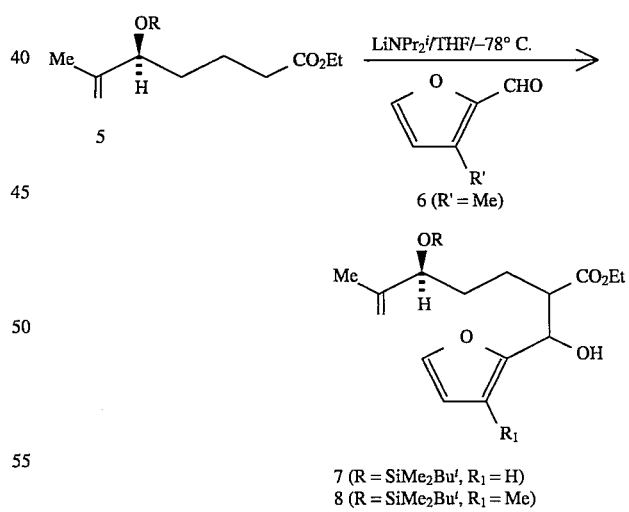

7 (R = SiMe$_2$Bu$^t$, R$_1$ = H)
8 (R = SiMe$_2$Bu$^t$, R$_1$ = Me)

Compound 9 (Scheme 5) is synthesized through condensation of compound 5 with any of a number of substituted furans. Where R$_1$ is methyl, the C-16/17 methyl of taxol is derived from the C-3 methyl group of the furan. Depending on the conditions, the substituent at the 2-position of the furan may either be an aldehyde or an ester. When an aldehyde furan is used reactions are typically run at −78° C.(CO$_2$-acetone). Where 2-substituted esters are used the reaction may be run at room temperature, e.g., in tetrahydrofuran at 25° C. If ring expansion takes place in the top half of the 7 membered ring precursors then the C-4 methyl group also becomes the C-16/17 methyl group. The methyl group may be replaced by alkyl, aryl, etc. Additionally, the aldol reaction may be performed in the presence of different amide bases where esters instead of furan aldehydes are used. Similar variations in the methyl group may be employed.

Scheme 5

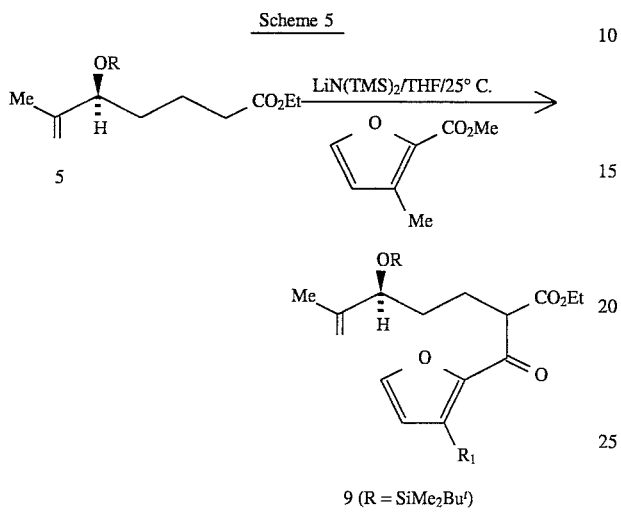

The reduction of compound 7 tp gove 10 (Scheme 6) is shown using lithium aluminum hydride in tetrahydrofuran but similar results are also obtained using lithium borohydride. The borohydride is the reagent of choice in the chiral series.

Scheme 6

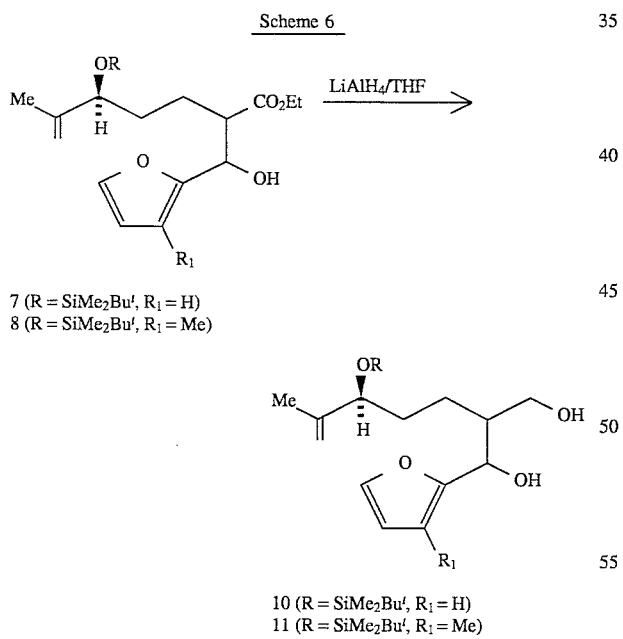

7 (R = SiMe₂Buᵗ, R₁ = H)
8 (R = SiMe₂Buᵗ, R₁ = Me)

10 (R = SiMe₂Buᵗ, R₁ = H)
11 (R = SiMe₂Buᵗ, R₁ = Me)

Selective protection of the hydroxyl group of compound 10 with the trityl group is shown in Scheme 7. The hydroxyl group may also be protected with tert-butyldimethylsilyl or any other commonly used alcohol protecting group. The protected furan compound 12 is conveniently oxidized to the pyranenone using singlet oxygen. Typically one would employ oxygen and a sensitizer such as Rose Bengal in the presence of light such as provided with a tungsten lamp (Scheme 8). t-Butylhydroperoxide/VO(acac)₂ can also be used to convert 12 into 14.

Scheme 7 (Tr = CPh₃)

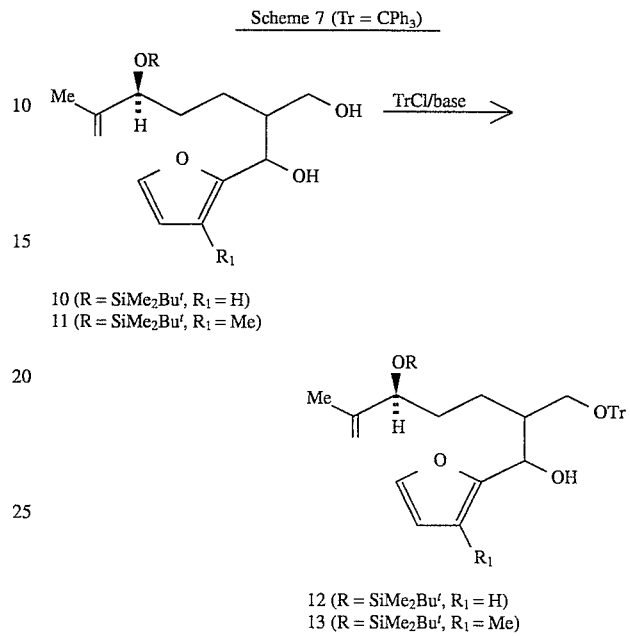

10 (R = SiMe₂Buᵗ, R₁ = H)
11 (R = SiMe₂Buᵗ, R₁ = Me)

12 (R = SiMe₂Buᵗ, R₁ = H)
13 (R = SiMe₂Buᵗ, R₁ = Me)

Scheme 8 (Tr = CPh₃)

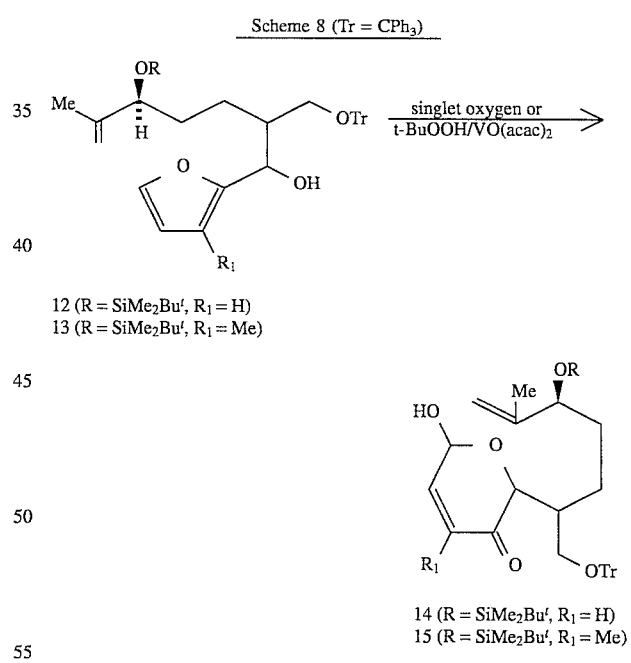

12 (R = SiMe₂Buᵗ, R₁ = H)
13 (R = SiMe₂Buᵗ, R₁ = Me)

14 (R = SiMe₂Buᵗ, R₁ = H)
15 (R = SiMe₂Buᵗ, R₁ = Me)

The conversion of 14/15 to the cycloheptenones 18,19,20, and 21 is readily accomplished by acetylation (Scheme 9). In preferred practice, acetic anhydride is used but other anhydrides may be used. The formation of the ylide and subsequent cyclization can be in toluene at temperatures ranging from 25°–110° C. Other solvents can be used such as dichloromethane, acetonitrile, dimethylformamide, tetrahydrofuran and so forth.

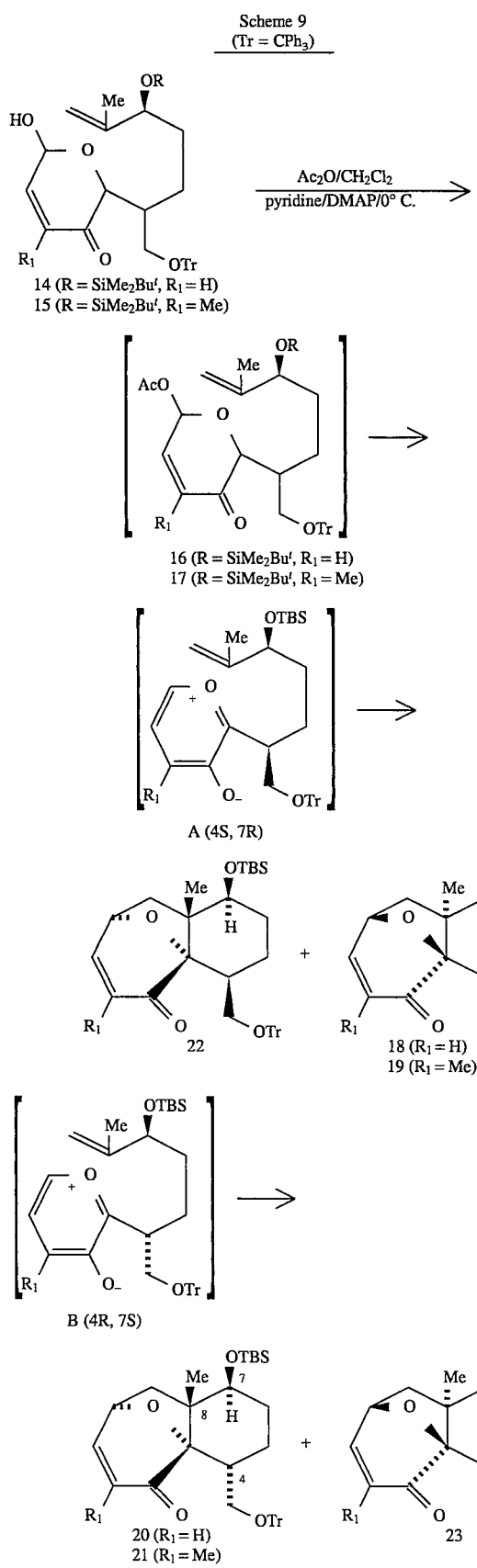

Scheme 9
(Tr = CPh₃)

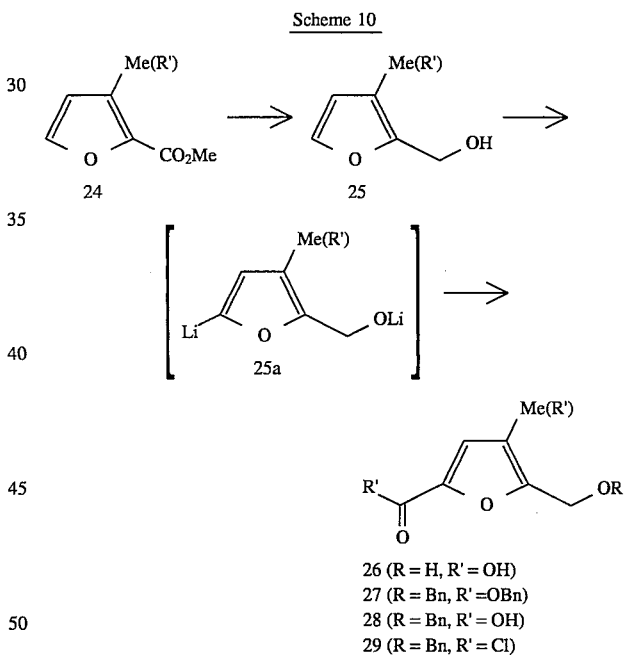

As is apparent, this synthetic scheme is readily adapted to the synthesis of a variety of cycloheptenones having the general structure shown in FIG. 2. Thus, the R, R', and R" groups can be methyl or virtually any alkyl or aryl group. PG represents a protecting group. While benzyl as protecting group is preferred, methoxy methyl (MOM) may also be used as well as substituted benzyl ethers such as 4-methoxybenzyl. Such syntheses are based on the use of a hydroxymethyl substituted furan.

The hydroxymethyl derivatives are obtained from furan esters such as compound 24 by reduction of the esters to the corresponding alcohol with a reducing agent such as lithium aluminum hydride, conversion into the dilithio derivative, e.g., with n-BuLi followed by a treatment with $CO_2$ to give an acid group at position 5 and conversion of the original ester into an alcohol group. The resulting hydroxyacid may be converted into the di-O-benzyl derivative and subsequently hydrolysed to the acid which may be converted into the acid chloride. This synthetic scheme allows variations at the OR group, e.g., OMOM. This is illustrated in Scheme 10.

Scheme 11 illustrates the inventors' synthetic scheme to provide the B and C rings of taxol in the appropriate and correct absolute configuration. This same sequence of reactions has also been used to make the 7-desoxy analogue. This is shown in Scheme 12.

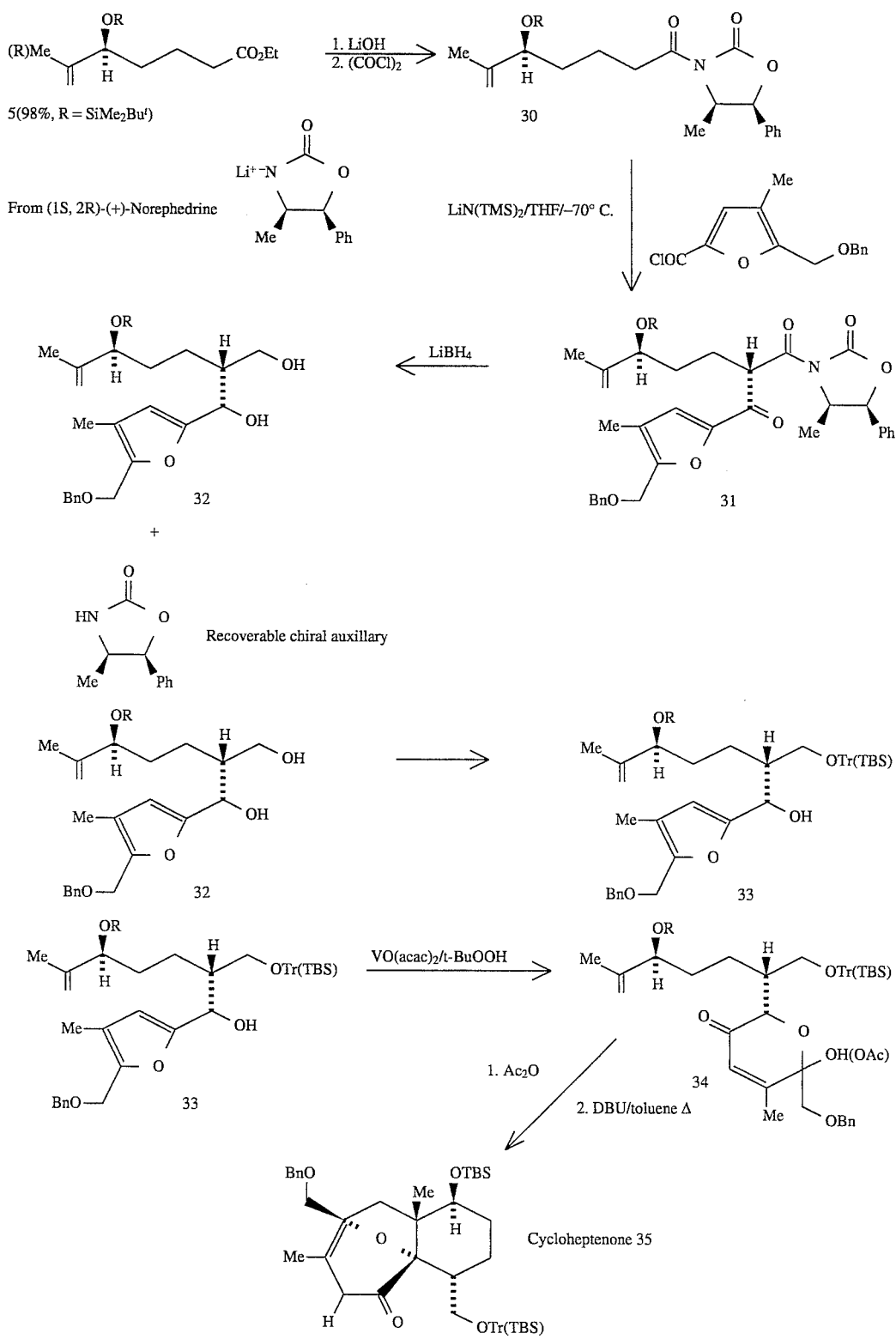
Scheme 11

Scheme 12

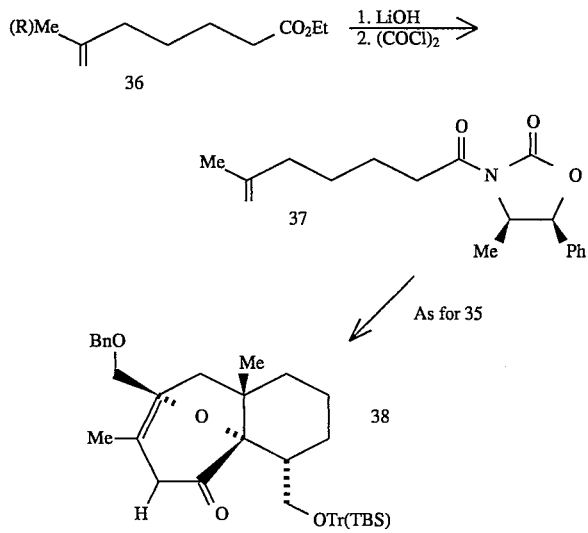

Different chiral auxiliaries may be used. In addition to the norephedrine illustrated, for example, phenylglycinol and other similar compounds as are known to those of skill in the art. In the example shown and as would be the case with other chiral auxiliaries, the chiral auxiliary can be recovered and recycled. The ester 5 is converted into the chiral amide 30 and subjected to a Claisen condensation reaction with the furan acid chloride 29 to give the intermediate 31 which is reduced in situ with lithium borohydride to give 32. The primary alcohol group in 32 is selectively protected as either a trityl or tertbutyldimethylsilyl ether to give 33. Oxidative rearrangement of 33 using the procedure shown or singlet oxygen provides the pyranenone 34. Acetylation and heating in toluene in the presence of DBU provides compound 35. A similar sequence of transformations may be carried out in the 7-desoxy series to give compound 38 (Scheme 12).

Ring expansion in the 7-deoxy series is shown in Schemes 13 and 14. Conjugate addition of MeMgBr catalyzed by $Cu^{II}$ gave 39. Use of ethyl, propyl, etc. Grignard reagents gives rise to different C-17 groups and may be used to provide other alkyl, vinyl, allyl, or aryl groups at this position. Removal of the alcohol protecting groups gave compound 40. Reductive cleavage of the C-O bond and intramolecular ketalization lead to compound 41. The primary alcohol may be activated by formation of the triflate derivative 42. Primary alcohol activation is not limited to use of the triflate group and other activating groups such as mesylate, tosylate and the like may be employed.

Scheme 13
(Ring expansion in the 7-deoxy series)

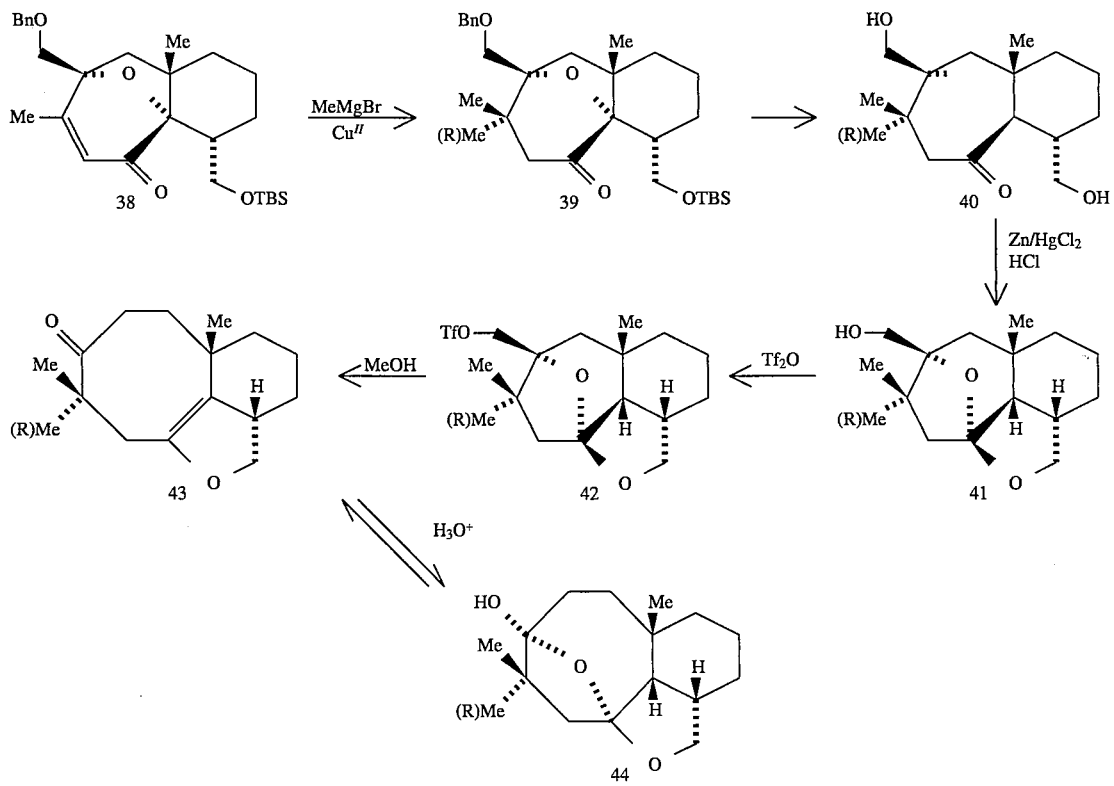

Scheme 14
(Ring expansion in the 7-deoxy series at a higher oxidation level)

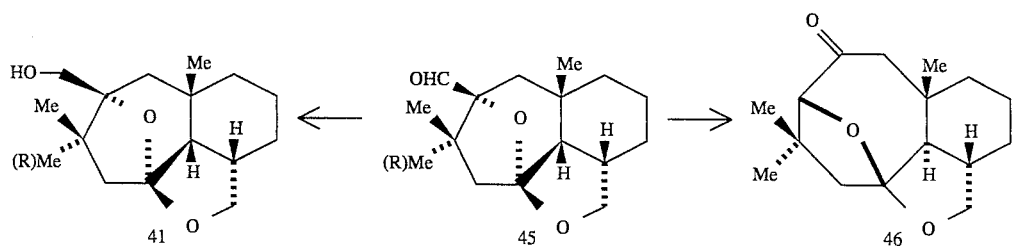

Solvolysis of compound 42 in a polar solvent such as methanol results in ring expansion of the 7 membered B ring to the 8 membered ring 43. While methanol is a preferred solvent, other alcohols may be used, including ethanol, propanol, butanol, isopropyl alcohol, and the like. The ketone 43 readily forms the ketal 44 on exposure to mildly acidic conditions.

In the 7-desoxy series, the alcohol 41 has been oxidized to the aldehyde 45 (Scheme 14). Upon treatment with boron trifluoride etherate, $BF_3 \cdot OEt_2$, 45 undergoes rearrangement to compound 46. Compound 46 has the correct trans fusion between the B and C rings.

The synthesis shown in Scheme 15 outlines a route that attaches the remaining A ring carbon atoms and allows for ring expansion without the necessity for reductive cleavage of the oxido bridge. Treatment of compound 39 with potassium bis(trimethylsilyl)amid/paraformaldehyde gives the enone 47. Conjugate addition of nitropropane to give 48 was accomplished using potassium carbonate in dimethylsulfoxide. While nitropropane was used to illustrate this synthesis, other nitroalkanes may be employed, thereby allowing versatility in having different substituents at the 12 position. Removal of the TBS protecting group in conversion of the nitro group into a carbonyl group (Nef reaction) gave 49.

Scheme 15

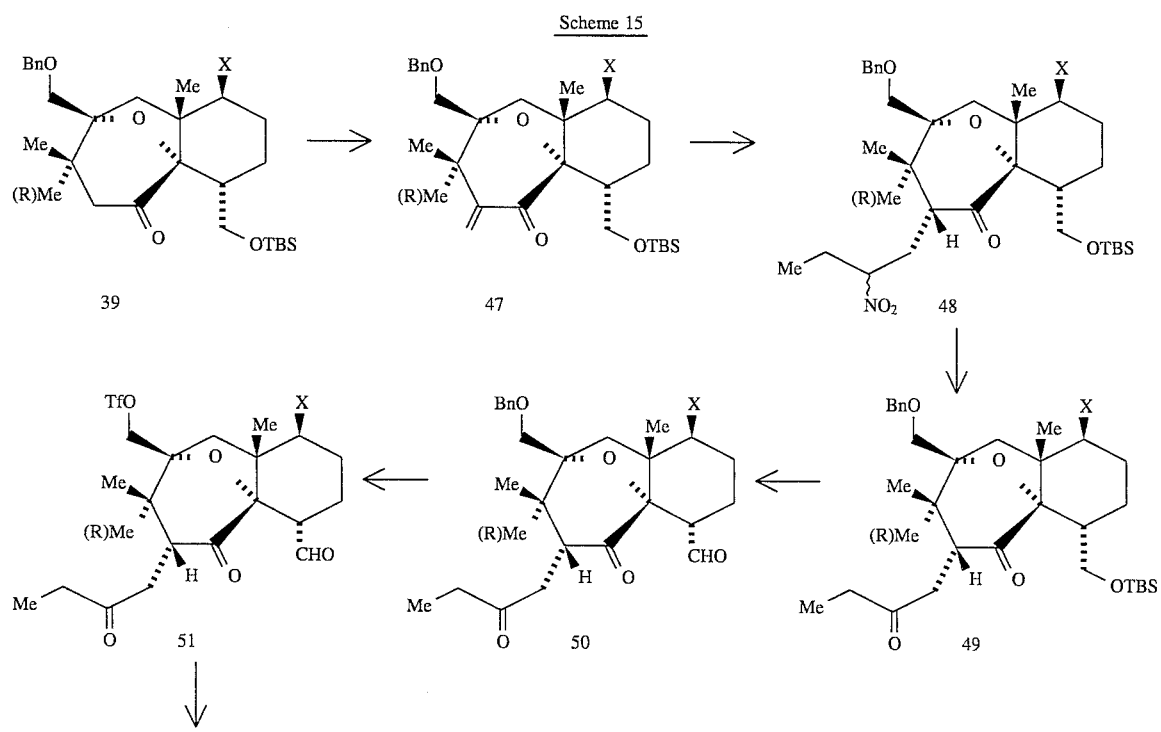

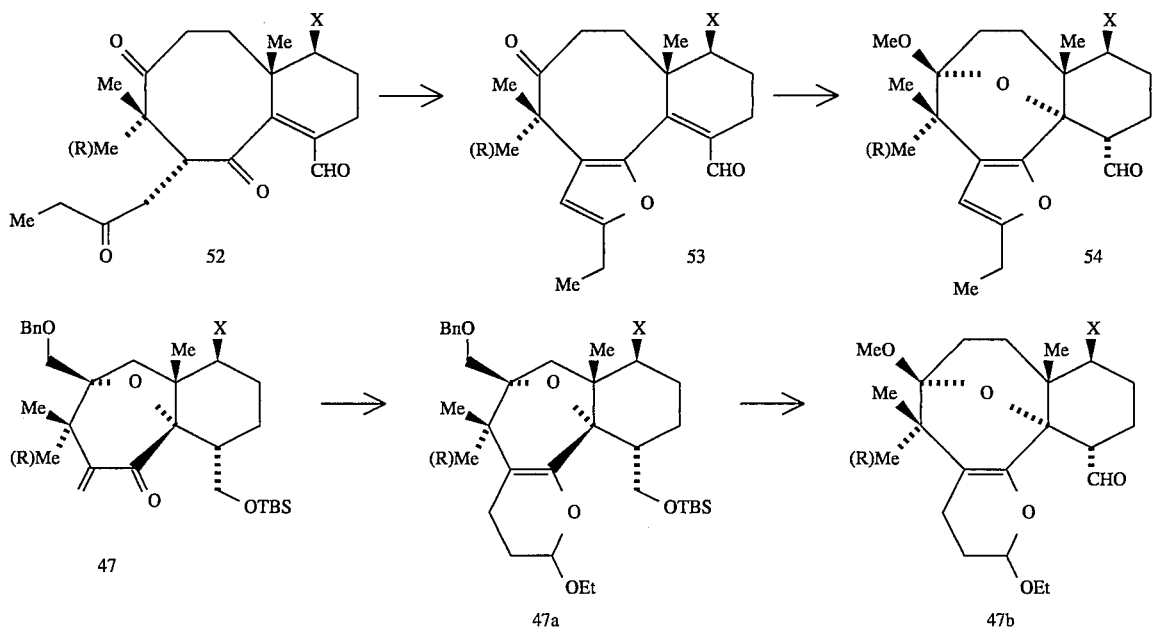

Oxidation of compound 49 provides the aldehyde 50. Hydrogenolysis of the benzyl ether followed by triflic anhydride gave the triflate 51. Treatment of 51 with methanol/ 2,6-di-tert-butyl-4-methylpyridine at 60° C. resulted in ring expansion to give the adduct of 52 which rapidly formed the furan 53 and eventually gave compound 54. The structure of compound 54 was confirmed by x-ray.

The furan ring can be formed prior to ring expansion, see Scheme 16. Treatment of 50 with p-toluenesulfonic acid in benzene gave the adduct 55. Hydrogenolysis, triflate formation and solvolysis in methanol gave 53, which was rapidly convert into 54. Solvolysis in other alcohol solvents such as ethanol may be employed.

Scheme 16

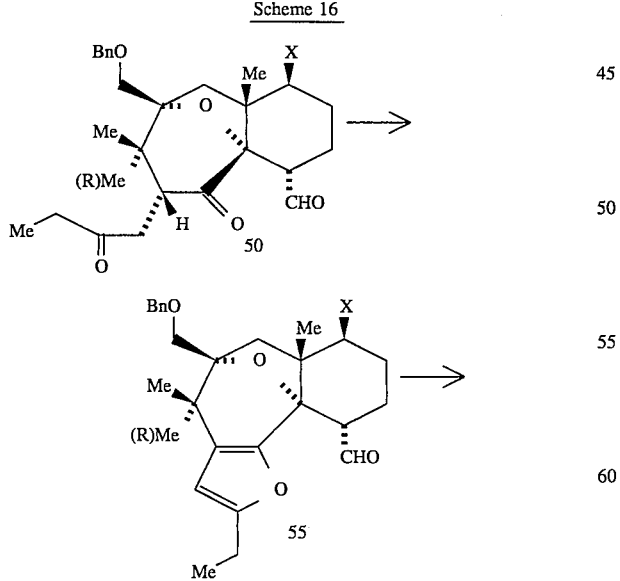

-continued
Scheme 16

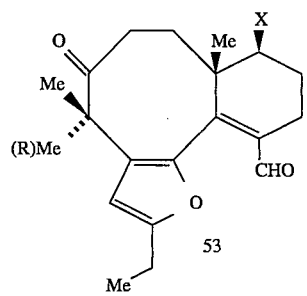

Scheme 17 further illustrates synthesis with different group substituents at C-12. As discussed, this is readily obtained by using different nitroalkane groups.

Scheme 17

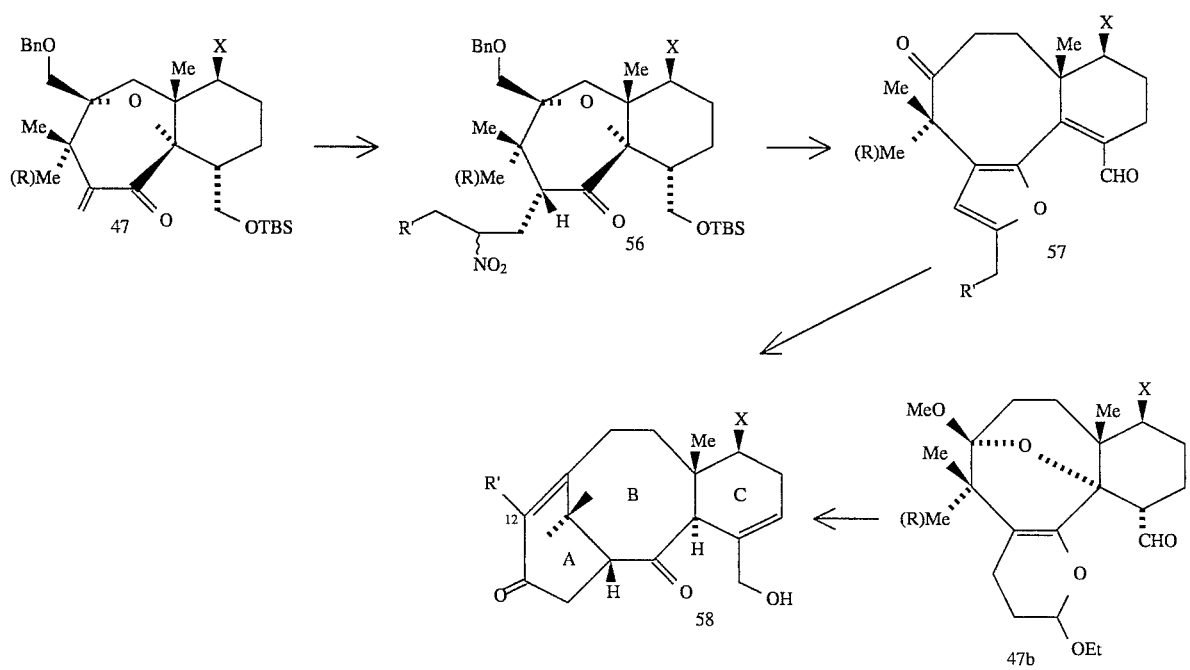

Scheme 17a

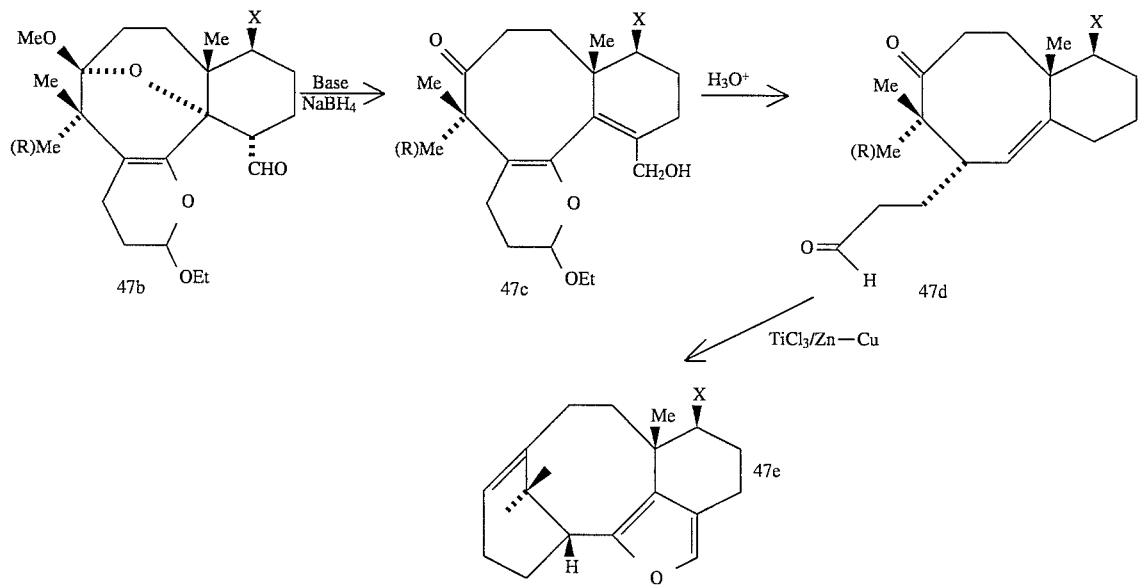

The shortest approach to the B/C and A/B/C ring system is by cyclopropane internal C-C bond cleavage. Scheme 18 shows that an activated enone such as 59 (CN can be replaced by —COMe, CO₂R) can be cyclopropanated to give the adduct 60. Treatment of 20 with bromine followed by sodium or potassium cyanide results in 59. The activated enone 59 is readily converted to 60 in 95% yield when exposed to isopropyltriphenylphosphorane.

Scheme 18

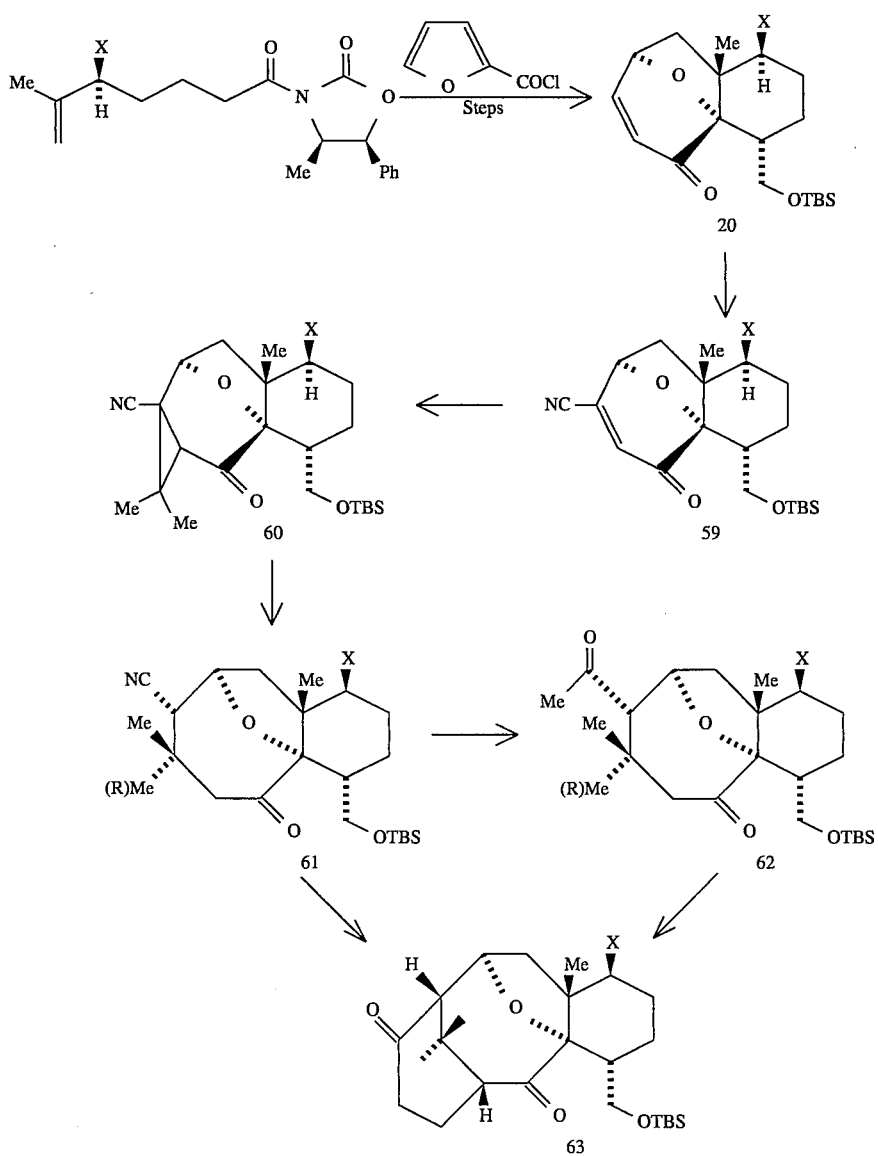

When 60 is exposed to reductive cleavage conditions (e.g., sodium naphthalenide/THF) the internal cyclopropane C-C bond is cleaved to give 61 in 95% yield. The structure and stereochemistry of 61 was obtained by X-ray crystallography. The nitrile 61 reacts with vinyl lithium to give, after acidic workup, the taxol precurser 63. Treatment of 62 with lithium diisopropylamide followed by Eschenmosers salt ($CH_2=NMe_2{}^+I^-$) and treatment of the resulting adduct with methyl iodide/acetonitrile, followed by titanium tetrachloride resulted in 63. This is a preferred route to the core taxane skeleton as it is an requires surprisingly few steps with high overall yields.

Overall, the synthetic procedures discussed allow key structural variations at the 7, 8, 12, 16, and 17 positions (FIG. 3) of the A,B and C rings of taxol. The synthesis provides an efficient and commercially viable route to the total synthesis of taxol and taxol-like compounds and, more importantly, a synthetic route to novel taxols and intermediates to provide access to second and third generation taxol derivatives.

The invention not only provides an efficient synthetic route to taxol and related compounds, but also gives access to taxol derivatives that may offer therapeutic advantages such as decreased toxicity. The inventors therefore contemplate that many of these compounds will be useful not only as important intermediates in the total synthesis of taxol but also as therapeutic agents themselves. Such compounds are readily formulated for use as pharmaceutical agents and may for example be prepared for oral or parenteral administration.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic saline and either added to 1000 mL of hypodermoclysis fluid or injected at the proposed site of infusion, (see, for example, "Remington's Pharmaceutical Sciences" 15th Edition, pages 1035–1038 and 1570–1580). Some variations in dosage will necessarily occur depending on the condition of the subject being treated. The person responsible for administration will in any event determine the appropriate dose for the individual subject.

Upon formulation, solutions will be administered in a manner compatible with the dosage formulation and in such amount as is therapeutically effective. The formulations are easily administered in a variety of dosage forms such as injectable solutions, as mentioned, or as drug release capsules, oral preparations and the like.

All such formulations, whether for oral or injectable administration, will of course be prepared so as to be "pharmaceutically acceptable", that is, with molecular entities and compositions that do not produce an allergic or similar untoward reaction when administered to a human.

DETAILED DESCRIPTION OF PREFERRED EMBODIMENTS

Figure 1A:
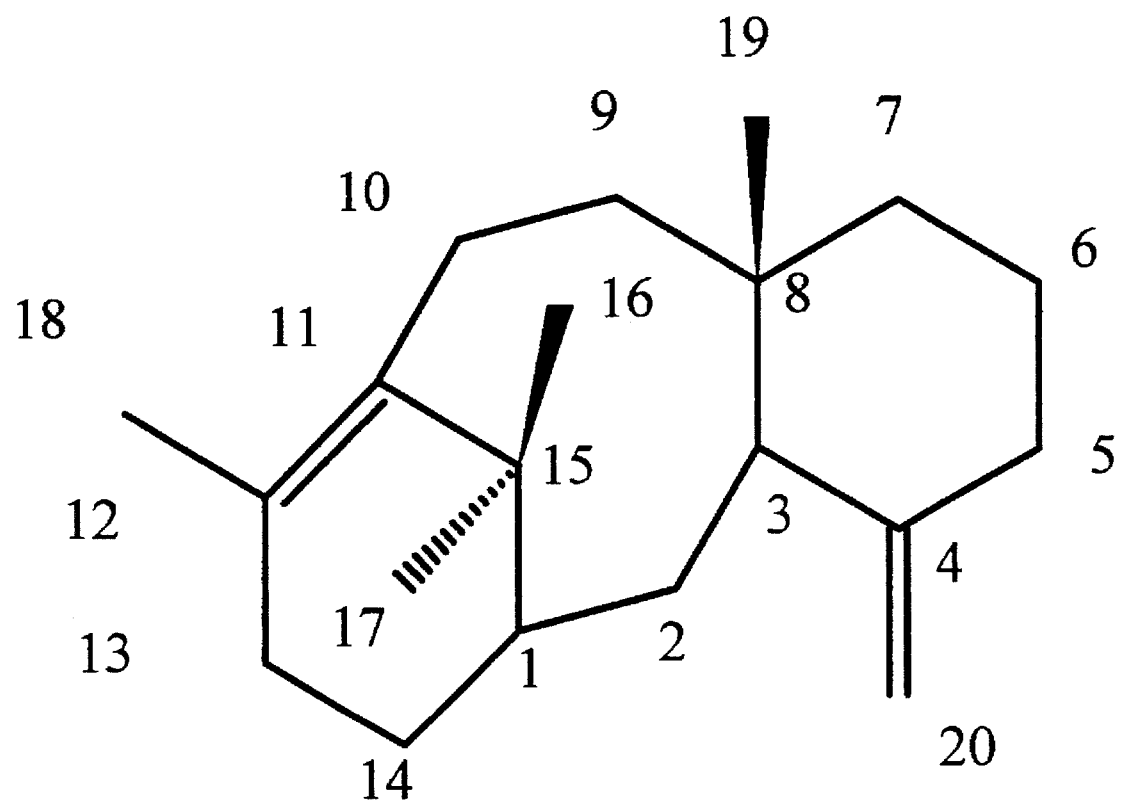
FIG. 1A shows the structure and numbering for the taxane ring system.

There are two important structure activity relation (SAR) features of taxol that should be taken into consideration in the synthetic design. The amino-alcohol side chain at C-13 is essential for antitumor activity (Ojima, et al., 1992; Farina, al., 1992; Georg, et al., 1992). Methods are known for the conversion of the C-13 alcohol into taxol (Denis, et al., 1988; Holton, 1991; Holton, 1992; Holton, 1993).

The oxetane, C-20, C-4 and C-5, also appears to be essential for full biological activity (Samaranayake, et al., 1991; Denis, et al., 1988). Simple model studies demonstrate that the oxetane functionality is readily constructed (Magee, et al., 1992; Berkowitz, et al., 1987; Lin, et al., 1987; Nicolaou, et al., 1992) and recent work has also described more complicated compounds with the oxetane intact (Kingston, et al., 1990).

In the following examples, two series of compounds are described; one with all the oxygen functionality and the other as the 7-desoxy series.

EXAMPLE 1

This example shows the strategy for the synthesis of a hydroxypyranenone which provided the basis for the stereoselective synthesis of the taxol core structure. The reactions are shown in Schemes 1 through 9 with numbers in the figure corresponding to the compounds whose synthesis is described.

The starting material was ethyl 6-methyl-5-oxo-6-heptanoate 3, comprising carbon atoms C-9, 8, 19, 7, 6, 5, 4 and 20 of the taxol core. The ester 3 is a known compound and is readily prepared on a large scale (354 g., 92%) by the bis (triphenylphosphine)palladium(II) chloride catalyzed coupling of methacryloyl chloride in toluene with the organozinc reagent 2 (Smith, et al., 1973; Tamaru, et al., 1988). Ethyl 4-bromobutyrate may be converted directly into ethyl 6-methyl-5-oxo- 6-heptanoate 3 (Jubert and Knochel, 1992), by conducting the above reaction in the presence of n-Bu$_4$N$^+$ I$^-$.

The C-5 carbonyl group is selectively reduced with sodium borohydride/cerium (III) chloride heptahydrate in ethanol to give (±)-ethyl 5-hydroxy-6-methyl-6-heptenoate 4 (265 g., 80%)(Luche, 1978). Both enantiomers of 4 are readily synthesized. Reduction of the C-5 carbonyl group with borane-dimethylsulfide in tetrahydrofuran in the presence of a catalytic amount of the chiral reagent (S)-(−)-diphenyl-2-pyrrolidino methanol oxaazaborole gave the 5R enantiomer of 4. (89%)(Corey, et al., 1987; Corey and Bakshi, 1990; Mathre, et al., 1991; Jones, et al., 1991). The enantiomeric excess is >93% as judged from the $^1$H NMR spectrum of the derived Mosher ester. The (R)-(−)-diphenyl-2-pyrrolidino methanol oxaazaborole catalyst gave the 5S enantiomer of 4, which corresponds to the natural absolute configuration of taxol at the C-7 secondary hydroxyl group. This route is not dependent upon a naturally occurring chiral starting material, thereby giving access to both enantiomers of the precursors. The chirality is introduced by reagents that are used in catalytic quantities.

The secondary hydroxyl group in 4 was protected as the t-butyl dimethylsilyl ether (TBS) by treatment with TBSOTf/NEtPr$^i_2$, to give 5 (98%); for example, other protecting groups are also suitable, e.g., methoxymethyl (MOM) ethers.

Treatment of 5 with lithium diisopropylamide in tetrahydrofuran at −78° C. followed by either 2-furfural or 3-methyl-2-furfural gave the aldol products 7 (98%) and 8 (100%) respectively. The aldol reaction gives two sets of diastereomers which can be separated. In the optically active series the stereochemistry at the furan carbinol is not important, but the newly created asymmetric carbon atom adjacent to the ethyl ester (C-4, taxol numering) controls the absolute stereochemistry at the quaternary methyl (C-8, taxol numbering). To control the absolute stereochemistry at C-4 (and eventually at C-8) the (1S, 2R)-(+)-norephedrine was used as a recyclable chiral auxiliary (Gage and Evans, 1989; Evans, et al., 1981; Evans, et al., 1981).

The same type of condensation at a higher oxidation level (Claisen-condensation) was conducted. Treatment of 5 and ethyl 3-methyl-2-furoate with lithium bis(trimethylsilyl) amide in treathydrofuran at 25° C. gave the β-keto ester 9 (>95%) as a mixture of diastereomers. Both diastereoisomers of 7, 8 and 9 were taken through the subsequent reactions for two purposes; first, to assess the stereochemical requirements of the intramolecular pyrylium-ylide cyclization in a relative and absolute stereochemical sense; secondly, to have access to unnatural seteroisomers of the taxol precursors for biological evaluation.

Figure 2:
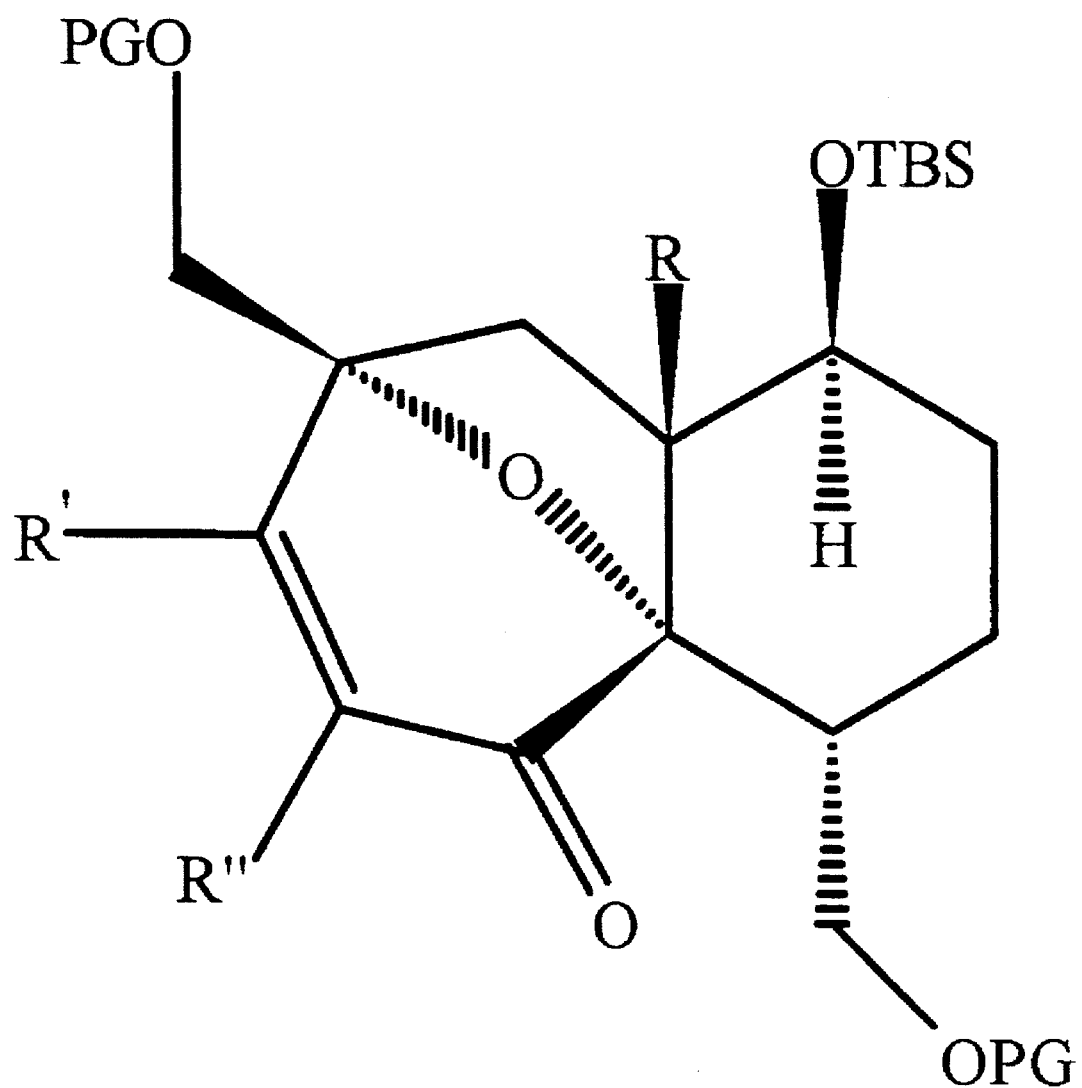
FIG. 2 shows several cycloheptenone compounds accessible from the disclosed synthesis, useful as key intermediates in the synthesis of taxol and taxol derivatives. The R, R' and R" groups are independently lower alkyl, aryl or hydrogen. Protecting groups (PG) are typically benzyl, methoxy methyl (MOM) or 4-methoxybenzyl.
Figure 3:
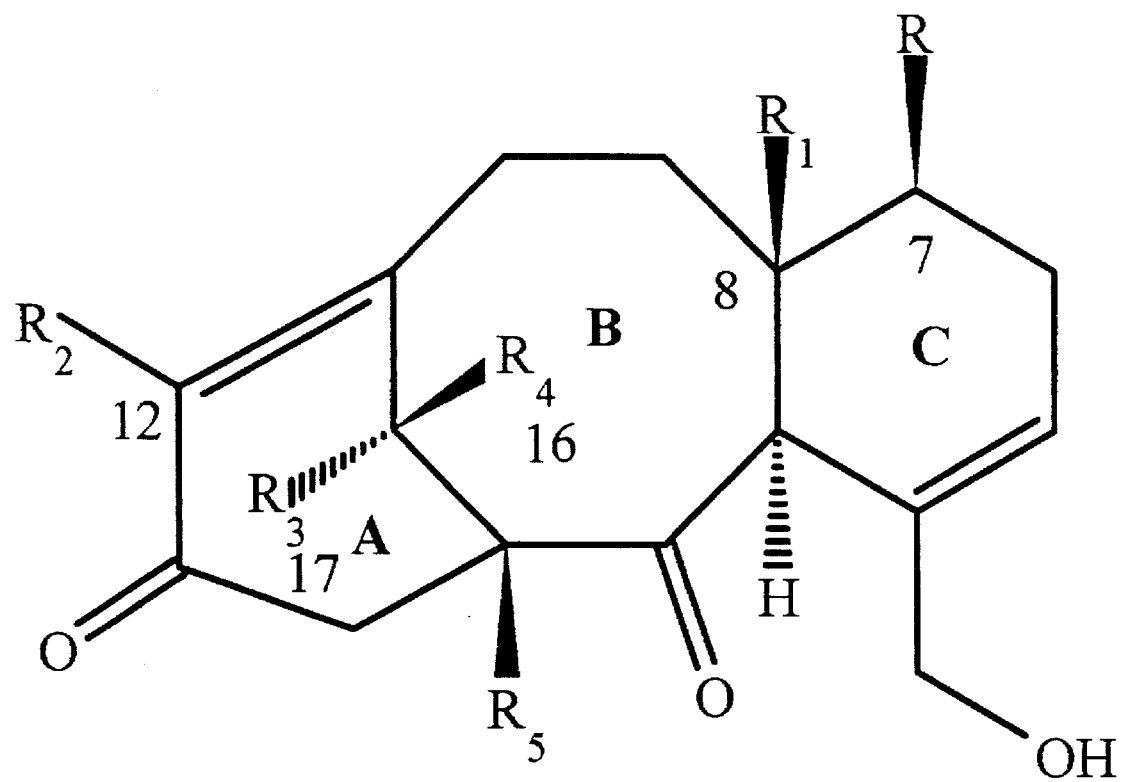
FIG. 3 shows the positions in the A,B and C rings of taxol where different groups can be substituted.

Only the natural absolute taxol stereochemistry is shown in FIG. 2, but it should be understood that all the diastereomers and their mirror images are readily separated to allow use in pure form rather than mixtures. The separation of the pure diastereomers in the optically active series is best carried out after the key pyrylium-ylide cyclization. The use of the chiral auxiliary approach in the 7-oxy series as described in Example 3 makes separation unnecessary, and a single optically active natural absolute stereochemistry versions of 20 and 21 becomes available.

Reduction of 7 using lithium aluminum hydride in tetrahydrofuran added at −78° C. and warmed to 25° C. gave 10 (99%). Similarly, reduction of 8 gave the methyl analog 11 (100%). The primary hydroxyl group in 10 and 11 was protected as the triphenyl methyl ether (trityl ether). Treatment of 10 with triphenylmethyl chloride in dichloromethane followed by triethylamine and 4-dimethylaminopyridine (DMAP, 0.1 equiv) gave the trityl ether 12 (97%). Similarly, the methyl analog 11 gave the corresponding trityl ether 13 (>90%). Other protecting groups for the primary alcohol can be used; for example, the primary t-butyldimethylsilyl ethers.

Oxidation of the furan carbinol 12 in dichloromethane with tert-butyl hydroperoxide in the presence of a catalytic amount of vanadyl acetyl-acetonate (Ho and Sapp, 1983) at −10° C. gave the rearranged hydroxypyranenone 14 (98%). The methyl analog 13 gave 15 in 98% yield.

The hydroxypyranenone 14 was converted into its derived acetate 16 by treatment with acetic anhydride in dichloromethane containing pyridine or triethylamine and a catalytic amount of 4-dimethylamino pyridine (DMAP). It is not necessary to purify the acetate since it can be used directly in the pyrylium ylide cyclization reaction.

EXAMPLE 2

Figure 1B:
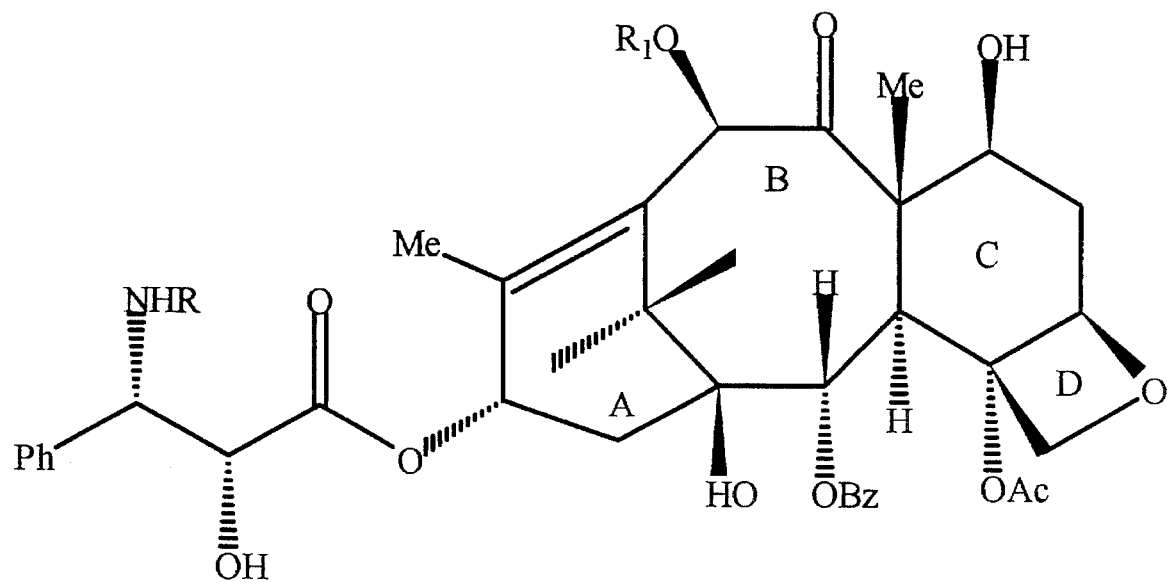
FIG. 1B shows the structure of taxol where Ac represents an acetate group and Bz a benzoyl group.

The key reactions for the synthesis of the core taxol structure are shown in Scheme 9. Results of this work indicated that the C-4 substituent stereochemistry controls the stereochemistry of the angular methyl group at C-8. The numbering system for taxol is shown in FIG. 1.
Pyrylium Ylide Cyclization.

The acetate 16 is a single stereoisomer at C-7 and a mixture at C-4. The other two stereogenic centers are destroyed in the conversion of 16 into the pyrylium ylide intermediate A/B. Therefore, in principle, heating 16 should give rise to the two pyrylium ylides A and B which can undergo intramolecular cycloaddition to give four products 18, 20, 22 and 23. In the racemic series the same compounds would be formed along with their mirror-image antipodes. The same situation prevails for the methyl analog series. Unexpectedly, heating 16 in dichloromethane or more rapidly in toluene in the presence of DBU gave only two cycloaddition productions 18 and 20 (65–85%) (Katritzky and Dennis, 1989). This result indicated that the C-4 substituent stereochemistry controls the stereochemistry of the angular methyl group C-8. The C-8 methyl group is always trans to the C-4 substituent. The methyl group at C-8 is also always trans to the oxygen bridge in the newly formed tetrahydrofuran ring in order to maintain the thermodynamically preferred cis fusion of this ring to the cyclohexane ring. This result was significant because it showed that of all the possible stereoisomers of 16, only one, namely the 4R, 7S diastereoisomer, gives the correct absolute stereochemistry at both C-7 and C-8.

In the racemic series the relative stereochemistry of 18 was established by single crystal X-ray crystallography. In the optically active series the absolute stereochemistry of the mirror image of 18 was established by single crystal X-ray crystallography of a derived camphanic acid ester.

Similarly in the methyl series heating 17 in the presence of DBU in dichloromethane or toluene gave 19 and 21 (65–85%). The isomers 18/20 and 19/21 can be separated by fractional crystallization or by chromatography of the detritylated derivatives. The tricyclic enone 21 contains carbon atoms C-2, 3, 4, 20, 5, 6, 7, 8, 19, 9, 10, 11, 15 and 16 (or 17) of the taxol core. The C-ring is intact, and the B-ring requires a one carbon ring expansion from a seven-membered ring to an eight-membered ring to complete the carbon skeleton.

Based on these results, a series of transformations was performed using a more elaborate furan that incorporates an extra carbon atom destined to become part of the eight-membered ring. These reactions are shown in Schemes 10–17. The known furan 24 was reduced with lithium aluminum hydride to give the derived alcohol 25. The alcohol 25 was treated with n-butyl lithium followed by carbon dioxide to give the acid 26. Treatment of 26 with benzyl bromide/sodium hydride/dimethylformamide gave 27 which was directly hydrolyzed to the acid 28 using sodium hydroxide in isopropanol. The acid 28 was converted into the acid chloride 29 by treatment with oxalyl-chloride (sodium salt).

The acid chloride 29 was treated with the lithium enolate derived from the amide 30 to give the adduct 31 which was reduced with lithium borohydride to give the diol 32 and the recoverable chiral auxiliary. The diol 32 was protected as the t-butyl dimethylsilyl ether 33 or trityl ether. (Scheme 11). The ether 33 was oxidized using tert-butyl hydroperoxide in the presence of a catalytic amount of vanadyl acetylacetonate (Ho and Sapp, 1983) at −10° C. to give the rearranged hydroxypyranenone 34. The hydroxypyranenone 34 was converted into its derived acetate by treatment with acetic anhydride in dichloromethane containing pyridine or triethylamine and a catalytic amount of 4-dimethylamino pyridine (DMAP). It was not necessary to purify the acetate since it could be used directly in the next stage. Heating the acetate in dichloromethane or more rapidly in toluene in the presence of DBU gave only two cycloaddition products 35 (79% from 31) and the diastereomer corresponding to 18/19. Only the diastereomer with the correct absolute configuration, namely 35 is shown. In the series with a chiral auxiliary, described in Example 3, the compound 35 was obtained as a single diastereomer and did not require any separation from unnatural stereoisomers.

EXAMPLE 3

A unique approach to synthesis of the taxol core structure is illustrated in this example. The results demonstrate that transannular interactions across the eight membered B ring of taxol are an intrinsic property of these structures.

Figure 4:
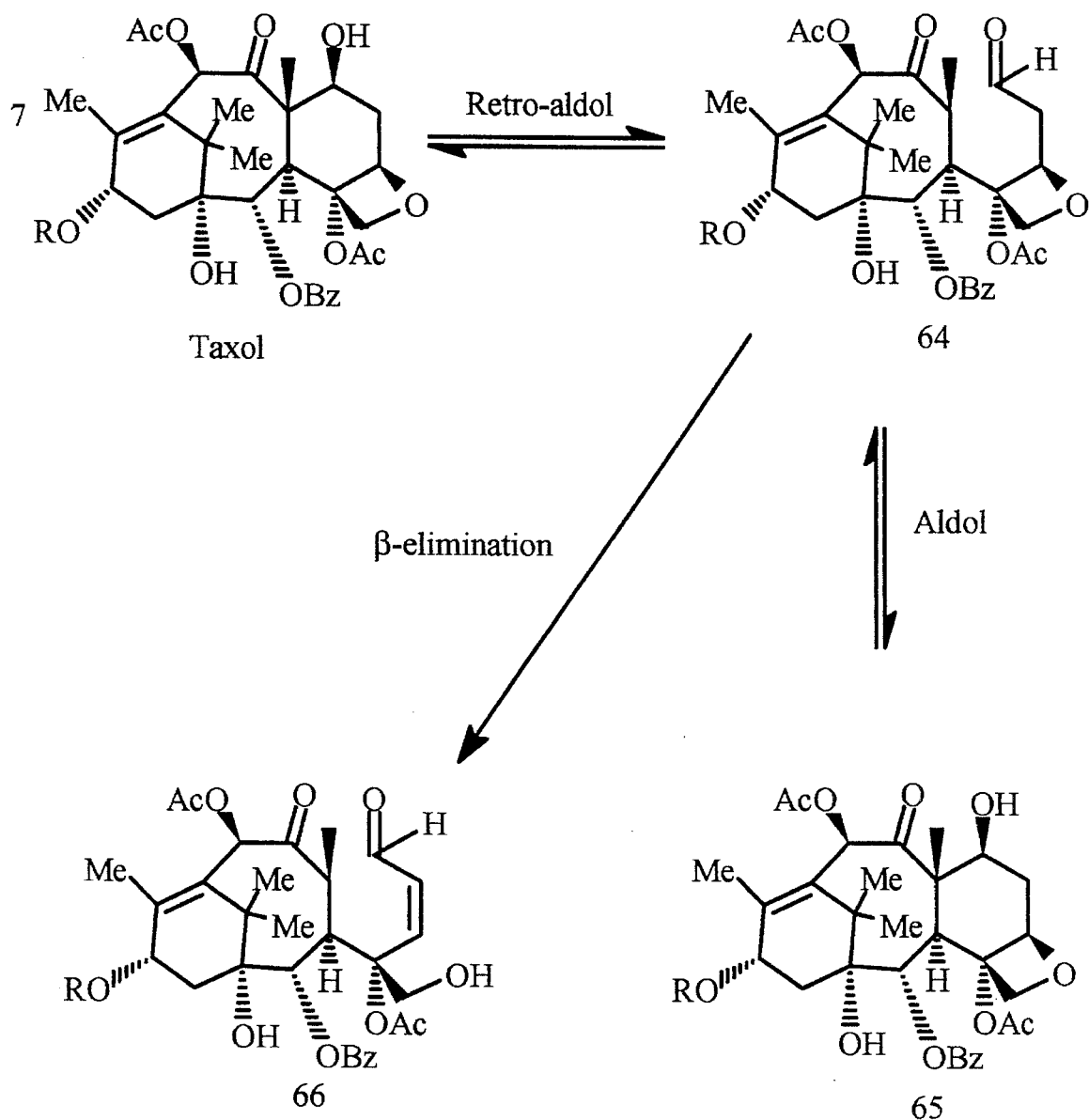
FIG. 4 shows the degradation of taxol.

Taxol is not a particularly potent antitumor drug, and it is suspected that it is extensively degraded before it reaches the target cells. A plausible pathway for its degradation is shown in FIG. 4. It involves the known reversible retro-aldol process that causes C-7 epimerization to give 65 via the aldehyde 64, and irreversible β-elimination of the C-5 oxetane C-O bond to the α,β-unsaturated aldehyde 66. Since it is known that the oxetane is necessary for activity this degradation would greatly reduce the potency of taxol. A way to prevent this process is to remove the C-7 hydroxyl group. Previous efforts to carry out this deoxygenation on taxol have failed. The only identifiable materials were ring B cleavage products. Consequently, 7-desoxytaxol 67 is a very important target for total synthesis.

Using the same strategy employed for the synthesis of 20/21 the methallyl chloride was converted into ethyl 6-methylhept-6-enoate 68 (70%). Conversion of 68 into 72 via 69, 70 and 71 utilizes the same chemistry as in the 7-hydroxy series. The reaction scheme is shown in Scheme 19. The same sequences of transformations can be carried out with the C-4 carbinol protected as a t-butyldimethylsilyl ether or a triisopropylsilyl ether. Other protecting groups can be used.

of the furan carbinol 74 in dichloromethane with tert-butyl hydroperoxide in the presence of a catalytic amount of vanadyl acetyl-acetonate at −10° C. gave the rearranged hydroxypyranenone 75 (90%). Treatment of 75 with acetic anhydride followed by heating the derived acetate in toluene

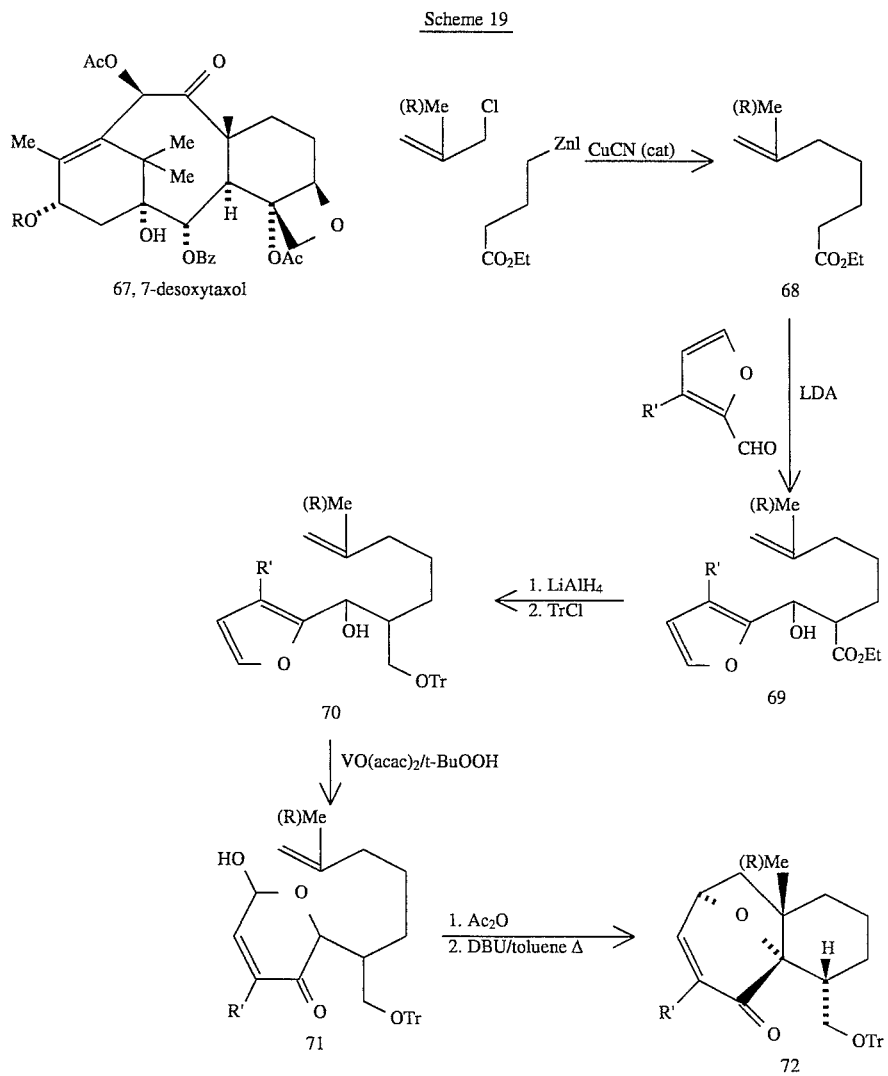

Scheme 19

Using the more elaborate furan 27a, the ester 68 was treated with lithium diisopropylamide and quenched with 27a to give 73. Scheme 20 illustrates the reaction scheme. Reduction of 73 using lithium aluminum hydride followed by protection of the primary hydroxyl group with t-butyldimethylsilyl chloride gave 74 (80% from 68). Oxidation in the presence of DBU gave 38 (64%). The additional methyl of the gem methyl group was introduced by treatment of 38 with methyl magnesium bromide in the presence of a catalytic amount of $CuBr.SMe_2$ in tetrahydrofuran to give 39 (75%).

Scheme 20

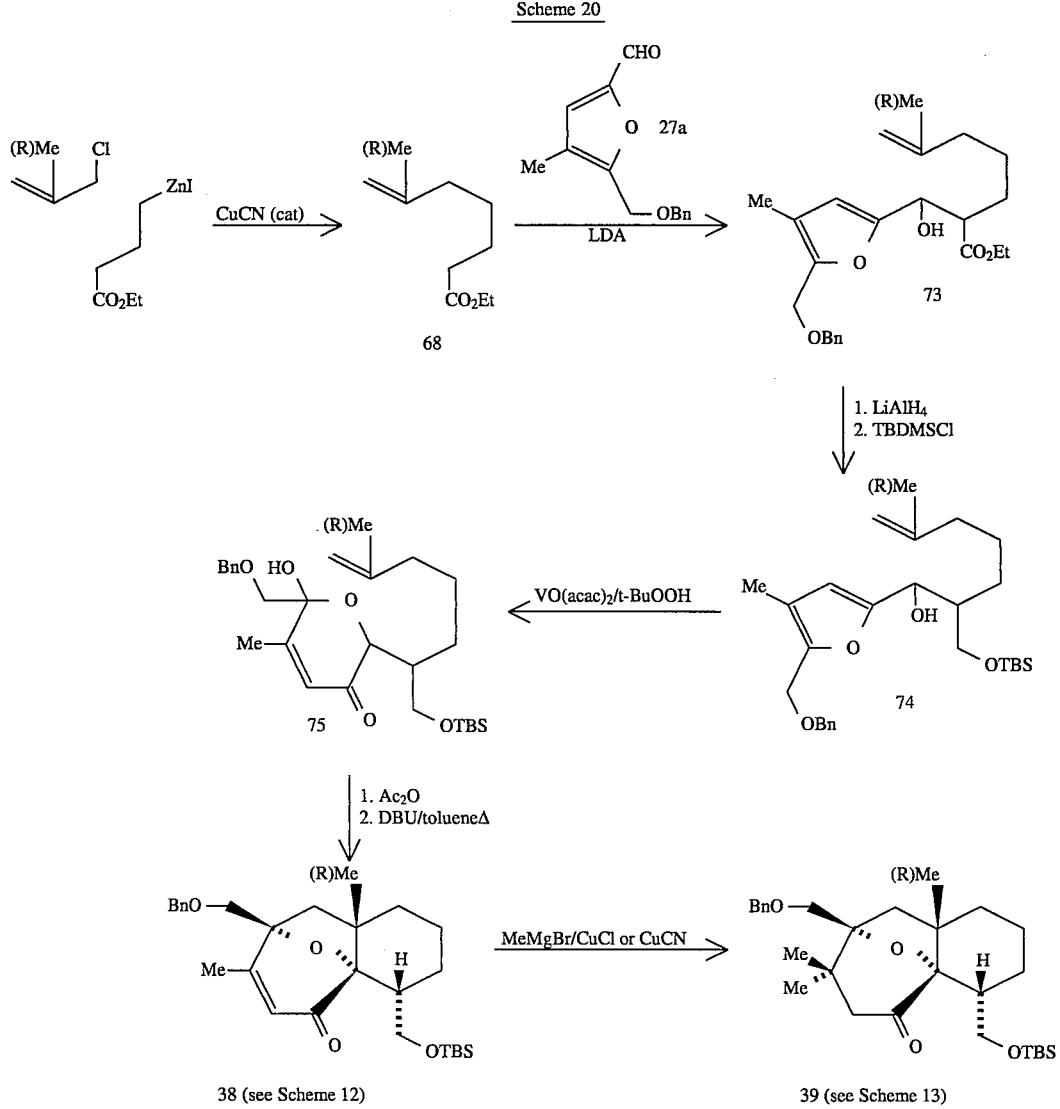

Hydrogenolysis and mild acid hydrolysis of 39 removed both the benzyl and t-butyldimethylsilyl ether protecting groups resulting in the diol 40. Treatment of 40 with Zn/HgCl$_2$/H$_3$O+ resulted in reductive cleavage of the oxido bridge and intramolecular ketalization to give 41 (80%). The carbinol 41 was converted into the trifluoromethanesulfonate derivative 42 by standard methods. Solvolysis of 42 in methanol resulted in ketal fragmentation, followed by ring expansion and proton loss, to give the eight-membered ring ketone 43. Exposure of 43 to aqueous acid gave the hemiketal hydrate 44, whose structure was confirmed by X-ray. Heating 44 converted it back into the ketone 43. These results revealed the advantage of differentiation of the two ketone carbonyl groups in 43 (Scheme 13).

The rearrangement may be carried out at a higher oxidation level to give a more functionalized eight-membered ring. Oxidation of the carbinol 44 using TPAP (cat)/NMNO (Griffith and Ley, 1990) gave the aldehyde 45, which upon treatment with BF$_3$OEt$_2$ resulted in rearrangement to give 46. The compound 46 has the C-10 ketone thereby enabling functionalization at C-9, and the correct trans B/C ring fusion (Scheme 14).

Control of Absolute Stereochemistry

To control the absolute stereochemistry at C-4 (and eventually at C-8), (1S, 2R)-(+)-norephedrine and R-(+)-phenylalanine were employed as recyclable chiral auxiliaries. Compound 30 (ee>90%) was synthesized using chiral Claisen technology (Evans, 1981). The amide in 31 was readily reduced using lithium borohydride in tetrahydrofuran to give the diol 32 and the recoverable chiral auxiliary. The reactions are shown in Scheme 11.

An identical sequence of transformations in the series with the C-7 hydroxyl substituent absent was carried out. (Scheme 18). Consequently, all of the compounds described in both antipodal forms (i.e. both natural and unnatural absolute stereochemistry) are accessible.

EXAMPLE 4

Scheme 21 outlines a total synthesis of the A/B/C ring system of taxol with the correct stereochemistry. The approach is based partly on the "cyclopropane" approach to ring expansion to the B/C rings. The entire sequence is 13 steps, starting from the relatively simple allyl ester shown in scheme 4.

Scheme 21 (Flow Chart for the Cyclopropane Approach, X = OTBS or H)

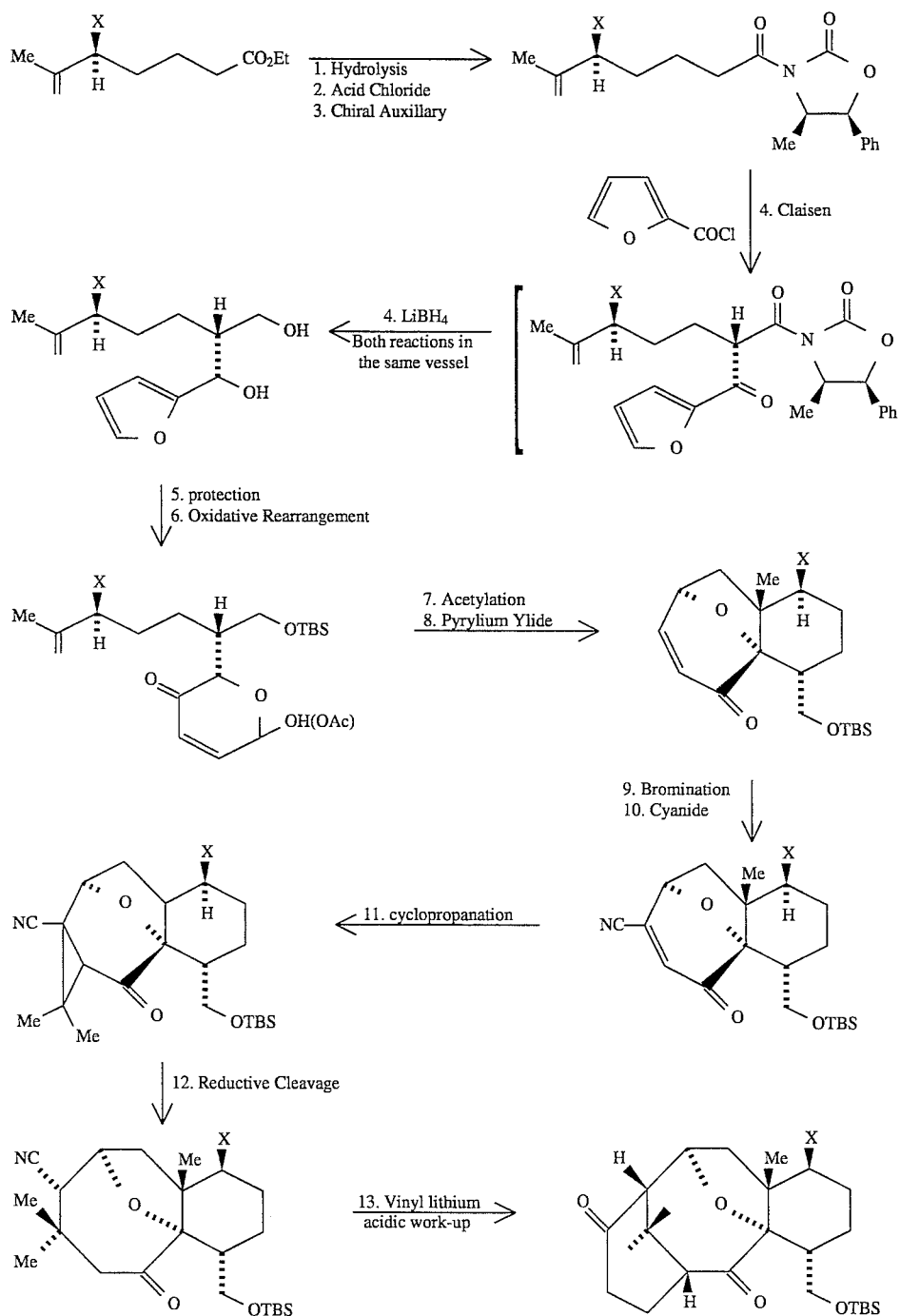

The overall route in scheme 21 comprises thirteen steps from the readily available heptenoate ester. Hydrolysis to an acid and activation of the acid by conversion into an acid chloride, followed by addition of the lithium salt of the chiral auxiliary resulted in the precursor in three steps. Claisen condensation and reduction in the same reaction vessel produced the diol which is protected on the primary alcohol and oxidatively rearranged to provide the pyrylium ylide precursor in three steps. Acetylation of the pyrylium ylide precursor, and heating in the presence of DBU, gave the cycloheptenone in two steps. Bromination of the cycloheptenone and treatment with cyanide anion resulted in the activated cyano-enone in two steps. Gem-methyl cyclopropanation and reductive cleavage of the internal cyclopropane bond resulted in ring expansion to form the eight-membered ring B of the taxol core skeleton in two steps. Finally, treatment of the eight membered-ring cyano compound with vinyl lithium followed by acidic workup formed the A-ring of taxol in one step.

The inventor has discovered that the fourth step in the synthesis providing the precursor diol is readily performed as a "one-pot" reaction. The Claisen condensation shown after step 3 need not be isolated but is treated directly with a reducing agent such as lithium borohydride to give the diol.

While the compositions and methods of this invention have been described in terms of preferred embodiments, it will be apparent to those of skill in the art that variations may be applied to the compositions, methods and in the steps or in the sequence of steps of the method described herein without departing from the concept, spirit and scope of the invention. More specifically, it will be apparent that the synthesis allows for a route to a wide variety of novel taxol related compounds and that modifications of the overall synthesis by well known procedures and reactions may be employed. All such similar substitutes and modifications apparent to those skilled in the art are deemed to be within the spirit, scope and concept of the invention as defined by the appended claims. All claimed matter and methods can be made and executed without undue experimentation.

REFERENCES

The following references to the extent that they provide exemplary procedural or other details supplementary to those set forth herein are specifically incorporated herein by reference.

Berkowitz, W. F., Amarasekara, A. S. and Perumattam, J. J., J. Org. Chem., 52, 1119, 1987.

Blechert, S. and Guénard, D., "Taxus Alkaloids", The Alkaloids, Ed. A. Brossi, Vol. 39, Ch. 6, 1990, Academic Press, NY.

Borman, S., "Scientists Mobilize to Increase Supply of Anticancer Drug Taxol", Chem. & Eng. News, Sep. 2nd, 1991.

Colin, M., Guénard, D., Guéritte-Voedelein, F. and Potier, P., Fr. Pat. Appl. 86/10,400, 1986; Eur. Pat. Appl. EP 253, 738, 1988.

Corey, E. J., Bakshi, R. K., Shibata, S., Chen, P. and Singh, V. K., J. Am. Chem. Soc., 109, 7925, 1987.

Corey E. J. and Bakshi, K., Tetrahedron Letters, 31, 611, 1990.

Denis, J. N., Greene, A. E., Guénard, D., Guéritte-Voegelein, F., Mangatal, L. and Potier, P., J. Am. Chem. Soc., 110, 5917, 1988.

Denis, J-N, Corea, A. and Greene, A. E., J. Org, Chem., 56, 6939, 1991 and references thereinEvans, D. A., Takacs, J. M., McGee, L. R., Ennis, M. D., Mathre, D. J. and Bartroli, J., Pure and App. Chem., 53, 1109, 1981.

Evans, D. A., Nelson, J. V., Vogel, E. and Taber, T. R., J. Am. Chem. Soc., 103, 3099, 1981.

Farina, V., Hauck, S. I. and Walker, D. G., Synlett, 761, 1992.

Gage, J. R. and Evans, D. A., Org. Synth., 68, 83, 1989, and 68, 77, 1989.

Georg, G. I., Mashava, P. M., Akgun, E. and Milsread, M. W., Tetrahedron Letters, 32, 3151, 1991.

Georg, G. I., Akgun, E., Mashava, P. M., Milsread, M., Ping, H., Wu, Z. and Vander Velde, D., Tetrahedron Letters, 33, 2111, 1992.

Griffith, W. P. and Ley, S. V., Aldrichimica Acta, Vol. 23, No. 1, 1990.

Hendrickson, J. B. and Farina, J. S., J. Org. Chem., 45, 3359, 1980.

Ho, T. L. and Sapp, S. G., Syn. Commun., 13(3), 207, 1983.

Holton, R. A., Eur. Pat. Appl. EP 400,971, 1990, U.S. Pat. No. 5,015,744, 1991.

Holton, R. A., U.S. Pat. No. 5,015,744 (1991).

Holton, R. A., U.S. Pat. No. 5,136,060 (1992).

Holton, R. A., U.S. Pat. No. 5,229,526 (1993)

Jones, T. K., Mohan, J. J., Xavier, L. C., Blacklock, T. J., Mathre, D. J., Sohar, p., Jones, E. T. T., Reamer, R. A., Roberts, F. E. and Grabowski, E. J. J., J. Org. Chem., 56, 763, 1991.

Jubert, C. and Knochel, P., J. Org. Chem., 57, 5425, 1992.

Katritzky, A. R. and Dennis, N., Chem. Rev., 89, 827, 1989.

Kingston, D. G. I., Samaranayake, G. and Ivey, C. A., "The Chemistry of Taxol, A Clinically Useful Anticancer Agent", J. Nat. Prodt., Vol. 53, 1, 1990.

Krucoff, C., "Unlocking the Secrets of Taxol", The Saturday Evening Post, (Sep./Oct., 1991).

Lin, J., Nikaido, M. M. and Clark, G., J. Org. Chem., 52, 3745, 1987.

Lipshutz, B. H., Comprehensive Organic Synthesis, Ed., B. M. Trost, Vol. 1, 1991. Pergamon Press.

Luche, J. L., J. Am. Chem. Soc., 100, 2226, 1978.

Lythgoe, B., "The Taxus Alkaloids", The Alkaloids, Ed. R. H. F. Manske, Vol. 10, Ch. 14, 1968, Academic Press, New York.

Magee, T. V., Bornmann, W. G., Isaacs, R. C. A. and Danishefsky, S. J., J. Org. Chem., 57, 3274, 1992.

Mangatal, L., Adeline, M. T., Guminard, D., Guéritte-Voedelein, F. and Potier, P., Tetrahedron, 45, 4177, 1989.

Mathre, D. J., Jones, T. K., Xavier, L. C., Blacklock, T. J., Reamer, R. A., Mohan, J. J., Jones, E. T. T., Hoogsteen, K., Baum, M. W. and Grabowski, E. J. J., J. Org. Chem., 56, 751, 1991.

Nicolaou, K. C., Hwang, C. K., Sorensen, E. J. and Clairborne, C. F., J. Chem. Soc. Chem. Commun., 1117, 1992.

Ojima, I., Habus, I., Zhao, M., Georg, G. I. and Jayasinghe, L. R., J. Org. Chem., 56, 1681, 1991.

Ojima, I., Habus, I., Zhao, M., Zucco, M., Park, Y. H., Sun, C. H. and Brigaud, T., Tetrahedron, 48, 6985, 1992.

Ojima, I., Fenoglio, I., Park, Y.H., Sun, C. M., Appendino, G., Pera, P. and Bernacki, R. J., J. Org. Chem. 59, 515, 1994.

Palomo, C., Arrieta, A., Cossio, F., Aizpurua, J. M., Mielgo, A. and Aurrekoetxea, N., Tetrahedron Letters, 31, 6429, 1990.

Pharmaceutical & Biotech Daily, Thursday, Apr. 21, 1994, p. 4.

Rowinsky, E. K., Cazenave, L. A. and Donebower, R. C., J. National Cancer Inst. Vol. 82, 1247, 1990.

Samaranayake, G., Magri, N. F., jitrangsri, C. and Kingston, D. G. I., J. Org. Chem., 56, 5114, 1991.

Sammes, P. G., Street, L. J., J. Chem. Soc., Chem. Comm., 1056, 1982.

Sammes, P. G., Street, L. J., J J. Chem. Soc., Chem. Comm., 666, 1983.

Science, 263, 911 (1994)

Smith, R. D., Simmons, H. E., Org. Synth., Collected Vol. 5, 855, 973.

Swindell, C. S., "Taxane Diterpene Synthesis Strategies. A Review", Organic preparations and procedures Int., 23 (4), 465, 1991.

Tamaru, Y., Ochai, H., Nakamura, T. and Yoshida, Z., Org. Synth., 67, 98, 1988.

Wender, p., Lee, H. Y., Wilhelm, R. S., Williams, P. D., J. Am. Chem. Soc., 117, 8954, 1989.

Ed. Winkler, J. D., "Total and Semi-synthetic Approaches to Taxol", Tetrahedron, Vol. 48, No. 34, 1992.

"Bark for Cancer's Bite", Time, Jul. 1st, 1991. "A New Cancer Drug May Extend Lives-At Cost of Rare Trees", The Wall Street Journal, Tuesday, Apr. 9th, 1991.
"Is a Tree Worth a Life", News Week, Aug. 5th, 1991.
"Loving Yew", Economist, Feb. 9th, 1991.

What is claimed is:

1. A method of synthesis of the A/B/C ring system of taxol having the structure I where X is H or OH and R, $R_1$ and $R_2$ are independently H or lower alkyl, comprising the steps;

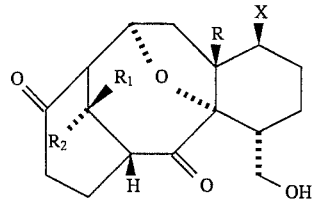

(a) reacting compound II by gem-alkyl cyclopropanation of the activated enone where EWG is a cyano, ester or aldehyde group, PG is an O-protecting group and R is H or lower alkyl;

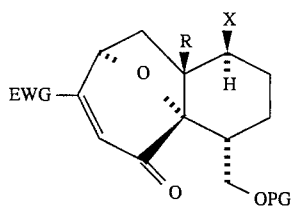

(b) to form the adduct III where $R_1$ and $R_2$ are independently H or lower alkyl;

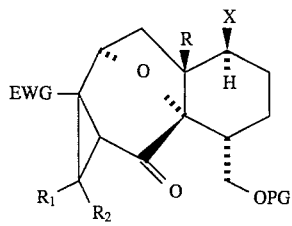

(c) cleaving the internal cyclopropane C-C bond of III under reducing conditions to form IV;

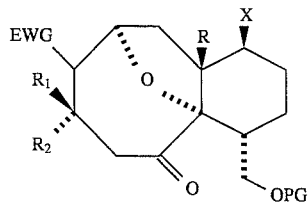

(d) adding a vinyl group to IV to form V; and

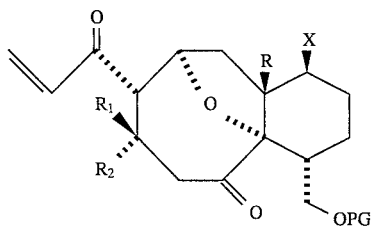

(e) treating V under acidic conditions to ring close and removing the O-protecting group to form I.

* * * * *